United States Patent
Gillies et al.

(10) Patent No.: US 7,790,415 B2
(45) Date of Patent: Sep. 7, 2010

(54) ENHANCING THE CIRCULATING HALF-LIFE OF ANTIBODY-BASED FUSION PROTEINS

(75) Inventors: Stephen D. Gillies, Carlisle, MA (US); Christa Burger, Darmstadt (DE); Kin-Ming Lo, Lexington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/360,682

(22) Filed: Jan. 27, 2009

(65) Prior Publication Data

US 2009/0264627 A1    Oct. 22, 2009

Related U.S. Application Data

(62) Division of application No. 11/268,191, filed on Nov. 7, 2005, now Pat. No. 7,507,406, which is a division of application No. 09/780,668, filed on Feb. 9, 2001, now Pat. No. 7,091,321.

(60) Provisional application No. 60/181,768, filed on Feb. 11, 2000.

(51) Int. Cl.
A61K 39/395 (2006.01)
C07K 16/46 (2006.01)
C12P 21/00 (2006.01)

(52) U.S. Cl. .............. 435/69.7; 424/134.1; 530/387.3

(58) Field of Classification Search .................. None
See application file for complete search history.

(56) References Cited

U.S. PATENT DOCUMENTS

| | | |
|---|---|---|
| 4,196,265 A | 4/1980 | Koprowski et al. |
| 4,469,797 A | 9/1984 | Albarella |
| 4,522,811 A | 6/1985 | Eppstein et al. |
| 4,667,016 A | 5/1987 | Lai et al. |
| 4,676,980 A | 6/1987 | Segal et al. |
| 4,703,008 A | 10/1987 | Lin |
| 4,732,683 A | 3/1988 | Georgiades et al. |
| 4,737,462 A | 4/1988 | Mark et al. |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,589,466 A | 12/1996 | Felgner et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |
| 5,728,552 A | 3/1998 | Fujisawa et al. |

(Continued)

FOREIGN PATENT DOCUMENTS

| | | |
|---|---|---|
| AU | 21725/88 | 3/1989 |
| CN | 93100115.3 | 7/1993 |
| DE | 37 12985 | 11/1988 |
| DE | 37 12985 A1 | 11/1988 |
| EP | 0 158 198 A1 | 10/1985 |
| EP | 0 211 769 A2 | 2/1987 |

(Continued)

OTHER PUBLICATIONS

Abaza et al., (1992), "Effects of Amino Acid Substitutions Outside an Antigenic Site on Protein Binding to Monoclonal Antibodies of Predetermined Specificity Obtained by Peptide Immunization," *Journal of Protein Chemistry*, 11:5:433-444.

(Continued)

*Primary Examiner*—David A Saunders
(74) *Attorney, Agent, or Firm*—Goodwin Procter LLP

(57) ABSTRACT

Disclosed are compositions and methods for enhancing the circulating half-life of antibody-based fusion proteins. Disclosed methods and compositions rely on altering the amino acid sequence of the junction region between the antibody moiety and the fused protein moiety in an antibody-based fusion protein. An antibody-based fusion protein with an altered amino acid sequence in the junction region has a greater circulating half-life when administered to a mammal. Disclosed methods and compositions are particularly useful for reducing tumor size and metastasis in a mammal.

42 Claims, 6 Drawing Sheets

U.S. PATENT DOCUMENTS

| | | | |
|---|---|---|---|
| 5,733,876 | A | 3/1998 | O'Reilly et al. |
| 5,738,852 | A | 4/1998 | Robinson et al. |
| 5,756,349 | A | 5/1998 | Lin |
| 5,756,461 | A | 5/1998 | Stephens |
| 5,759,551 | A | 6/1998 | Ladd et al. |
| 5,770,195 | A | 6/1998 | Hudziak et al. |
| 5,795,779 | A | 8/1998 | McCormick et al. |
| 5,800,810 | A | 9/1998 | Doyle et al. |
| 5,807,715 | A | 9/1998 | Morrison et al. |
| 5,827,516 | A | 10/1998 | Urban et al. |
| 5,827,703 | A | 10/1998 | Debs et al. |
| 5,837,682 | A | 11/1998 | Folkman et al. |
| 5,837,821 | A | 11/1998 | Wu et al. |
| 5,843,423 | A | 12/1998 | Lyman et al. |
| 5,854,205 | A | 12/1998 | O'Reilly et al. |
| 5,856,298 | A | 1/1999 | Strickland |
| 5,858,347 | A | 1/1999 | Bauer et al. |
| 5,885,795 | A | 3/1999 | O'Reilly et al. |
| 5,886,178 | A | 3/1999 | Allen et al. |
| 5,888,772 | A | 3/1999 | Okasinski et al. |
| 5,888,773 | A | 3/1999 | Jost et al. |
| 5,891,680 | A | 4/1999 | Lieschke et al. |
| 5,908,626 | A | 6/1999 | Chang et al. |
| 5,922,685 | A | 7/1999 | Rakhmilevich et al. |
| 5,955,422 | A | 9/1999 | Lin |
| 5,994,104 | A | 11/1999 | Anderson et al. |
| 5,994,126 | A | 11/1999 | Steinman et al. |
| 6,080,409 | A | 6/2000 | Laus et al. |
| 6,086,875 | A | 7/2000 | Blumberg et al. |
| 6,100,387 | A | 8/2000 | Herrmann et al. |
| 6,169,070 | B1 | 1/2001 | Chen et al. |
| 6,171,588 | B1 | 1/2001 | Carron et al. |
| 6,231,536 | B1 | 5/2001 | Lentz |
| 6,277,375 | B1 | 8/2001 | Ward |
| 6,281,010 | B1 | 8/2001 | Gao et al. |
| 6,284,536 | B1 | 9/2001 | Morrison et al. |
| 6,291,158 | B1 | 9/2001 | Winter et al. |
| 6,335,176 | B1 | 1/2002 | Inglese et al. |
| 6,340,742 | B1 | 1/2002 | Burg et al. |
| 6,348,192 | B1 | 2/2002 | Chan et al. |
| 6,406,689 | B1 | 6/2002 | Falkenberg et al. |
| 6,429,199 | B1 | 8/2002 | Krieg et al. |
| 6,444,792 | B1 | 9/2002 | Gray et al. |
| 6,475,717 | B1 | 11/2002 | Enssle et al. |
| 6,485,726 | B1 | 11/2002 | Blumberg et al. |
| 6,500,641 | B1 | 12/2002 | Chen et al. |
| 6,506,405 | B1 | 1/2003 | Desai et al. |
| 6,551,592 | B2 | 4/2003 | Lindhofer et al. |
| 6,583,272 | B1 | 6/2003 | Bailon |
| 6,586,398 | B1 | 7/2003 | Kinstler et al. |
| 6,617,135 | B1 | 9/2003 | Gillies et al. |
| 6,627,615 | B1 | 9/2003 | Debs et al. |
| 6,646,113 | B1 | 11/2003 | Dreyfuss et al. |
| 6,750,329 | B1 | 6/2004 | Rosenblum et al. |
| 6,838,260 | B2 | 1/2005 | Gillies et al. |
| 6,900,292 | B2 | 5/2005 | Sun et al. |
| 6,969,517 | B2 | 11/2005 | Gillies et al. |
| 6,992,174 | B2 | 1/2006 | Gillies et al. |
| 7,067,110 | B1 | 6/2006 | Gillies et al. |
| 7,091,321 | B2 | 8/2006 | Gillies et al. |
| 7,141,651 | B2 | 11/2006 | Gillies et al. |
| 7,148,321 | B2 | 12/2006 | Gillies et al. |
| 7,169,904 | B2 | 1/2007 | Gillies et al. |
| 7,186,804 | B2 | 3/2007 | Gillies et al. |
| 7,211,253 | B1 | 5/2007 | Way |
| 7,217,798 | B2 | 5/2007 | Hinton et al. |
| 7,226,998 | B2 | 6/2007 | Gillies et al. |
| 7,323,549 | B2 | 1/2008 | Lauder et al. |
| 7,432,357 | B2 | 10/2008 | Gillies |
| 7,459,538 | B2 | 12/2008 | Gillies et al. |
| 7,462,350 | B2 | 12/2008 | Gillies et al. |
| 7,465,447 | B2 | 12/2008 | Gillies et al. |
| 7,507,406 | B2 | 3/2009 | Gillies et al. |
| 7,517,526 | B2 | 4/2009 | Gillies et al. |
| 2001/0053539 | A1 | 12/2001 | Lauffer et al. |
| 2002/0037558 | A1 | 3/2002 | Lo et al. |
| 2002/0081664 | A1 | 6/2002 | Lo et al. |
| 2002/0142374 | A1 | 10/2002 | Gallo et al. |
| 2002/0146388 | A1 | 10/2002 | Gillies |
| 2002/0147311 | A1 | 10/2002 | Gillies et al. |
| 2002/0192222 | A1 | 12/2002 | Blumberg et al. |
| 2002/0193570 | A1 | 12/2002 | Gillies et al. |
| 2003/0003529 | A1 | 1/2003 | Bayer |
| 2003/0012789 | A1 | 1/2003 | Blumberg et al. |
| 2003/0044423 | A1 | 3/2003 | Gillies et al. |
| 2003/0049227 | A1 | 3/2003 | Gillies et al. |
| 2003/0105294 | A1 | 6/2003 | Gillies et al. |
| 2003/0139365 | A1 | 7/2003 | Lo et al. |
| 2003/0139575 | A1 | 7/2003 | Gillies |
| 2003/0157054 | A1 | 8/2003 | Gillies et al. |
| 2003/0166163 | A1 | 9/2003 | Gillies |
| 2003/0166877 | A1 | 9/2003 | Gillies et al. |
| 2004/0013640 | A1 | 1/2004 | Zardi et al. |
| 2004/0033210 | A1 | 2/2004 | Gillies |
| 2004/0043457 | A1 | 3/2004 | Schumacher et al. |
| 2004/0053366 | A1 | 3/2004 | Lo et al. |
| 2004/0072299 | A1 | 4/2004 | Gillies et al. |
| 2004/0082039 | A1 | 4/2004 | Gillies et al. |
| 2004/0180035 | A1 | 9/2004 | Gillies et al. |
| 2004/0203100 | A1 | 10/2004 | Gillies et al. |
| 2005/0042729 | A1 | 2/2005 | Lo et al. |
| 2005/0069521 | A1 | 3/2005 | Gillies et al. |
| 2005/0137384 | A1 | 6/2005 | Gillies et al. |
| 2005/0164352 | A1 | 7/2005 | Lauder et al. |
| 2005/0192211 | A1 | 9/2005 | Gillies et al. |
| 2005/0202021 | A1 | 9/2005 | Gillies |
| 2005/0202538 | A1 | 9/2005 | Gillies et al. |
| 2005/0244418 | A1 | 11/2005 | Gillies et al. |
| 2005/0261229 | A1 | 11/2005 | Gillies et al. |
| 2006/0025573 | A1 | 2/2006 | Gillies et al. |
| 2006/0034836 | A1 | 2/2006 | Gillies et al. |
| 2006/0141581 | A1 | 6/2006 | Gillies et al. |
| 2006/0194952 | A1 | 8/2006 | Gillies et al. |
| 2006/0228332 | A1 | 10/2006 | Gillies et al. |
| 2006/0263856 | A1 | 11/2006 | Gillies et al. |
| 2007/0036752 | A1 | 2/2007 | Gillies et al. |
| 2007/0059282 | A1 | 3/2007 | Gillies et al. |
| 2007/0104689 | A1 | 5/2007 | Gillies et al. |
| 2007/0154453 | A1 | 7/2007 | Webster et al. |
| 2007/0154473 | A1 | 7/2007 | Super et al. |
| 2007/0178098 | A1 | 8/2007 | Way et al. |
| 2007/0258944 | A1 | 11/2007 | Gillies et al. |
| 2007/0287170 | A1 | 12/2007 | Davis et al. |
| 2008/0025947 | A1 | 1/2008 | Gillies et al. |
| 2008/0311655 | A1 | 12/2008 | Gillies et al. |
| 2009/0010875 | A1 | 1/2009 | Lauder et al. |
| 2009/0088501 | A1 | 4/2009 | Qiu et al. |
| 2009/0092607 | A1 | 4/2009 | Gillies et al. |
| 2009/0098609 | A1 | 4/2009 | Gillies et al. |

FOREIGN PATENT DOCUMENTS

| | | |
|---|---|---|
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |

| | | |
|---|---|---|
| EP | 0 511 747 A1 | 11/1992 |
| EP | 0 519 596 A1 | 12/1992 |
| EP | 0 344 134 B1 | 1/1994 |
| EP | 0 601 043 B1 | 6/1994 |
| EP | 0 640 619 A1 | 3/1995 |
| EP | 0 668 353 A1 | 8/1995 |
| EP | 0 428 596 B1 | 4/1996 |
| EP | 0 706 799 A2 | 4/1996 |
| EP | 0 428 267 B1 | 12/1996 |
| EP | 0 790 309 A1 | 8/1997 |
| EP | 0 433 827 B1 | 3/1998 |
| EP | 0 668 351 B1 | 9/1999 |
| EP | 1 088 888 A1 | 4/2001 |
| EP | 0 699 755 B1 | 4/2004 |
| GB | 2 188 638 A | 10/1987 |
| GB | 2 292 382 A | 2/1996 |
| JP | 63-267278 | 11/1988 |
| JP | 63-267296 | 11/1988 |
| WO | WO 96/08570 | 3/1966 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/52976 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 | 12/2000 |
| WO | WO 01/07081 | 2/2001 |
| WO | WO 01/10912 | 2/2001 |
| WO | WO 01/36489 A2 | 5/2001 |
| WO | WO 01/58957 A2 | 8/2001 |
| WO | WO 02/02143 A2 | 1/2002 |
| WO | WO 02/066514 A2 | 8/2002 |
| WO | WO 02/072605 A2 | 9/2002 |
| WO | WO 02/079232 A2 | 10/2002 |
| WO | WO 02/079415 A2 | 10/2002 |
| WO | WO 02/090566 A2 | 11/2002 |
| WO | WO 03/015697 | 2/2003 |
| WO | WO 03/048334 A2 | 6/2003 |
| WO | WO 03/077834 A2 | 9/2003 |

OTHER PUBLICATIONS

Abstract XP-002116766, (1996), "Prostaglandins, their inhibitors and cancer," *Prostaglandins, Leukotrienes and Essential Fatty Acids*, 54:2:83-94.

Afonso et al., (1994), "The Adjuvant Effect of Interleukin-12 in a Vaccine Against Leishmania Major," *Science*, 263:235-237.

Arenberg et al. (1996), "Interferon-γ-inducible Protein 10 (IP-10) Is an Angiostatic Factor That Inhibits Human Non-small Cell Lung Cancer (NSCLC) Tumorigenesis and Spontaneous Metastases," *J. Exp. Med*, 184:981-992.

Bacha et al., (1988), "Interleukin 2 Receptor-Targeted Cytotoxicity Interleukin 2 Receptor-mediated Action of a Diphtheria Toxin-related Interleukin 2 Fusion Protein," *J. Experimental Medicine*, 167:612-622.

Bachelot et al., (Mar. 1998), "Retrovirus-Mediated Gene Transfer of an Angiostatin-Endostatin Fusion protein with Enhanced Anti-Tumor Properties In Vivo," *Proceedings of the Annual Meeting of the American Association for Cancer Research*, 39:271, Abstract #1856.

Barnett et al., (1994), "Purification, characterization and selective inhibition of human prostaglandin G/H synthase 1 and 2 expressed in the baculovirus system," *Biochimica et Biophysica Acta*, 1209:130-139.

Baselga, et al., (1998), "Recombinant Humanized Anti-HER2 Antibody (Herceptin™) Enhances the Antitumor activity of Paclitaxel and Doxorubicin against HER3/*neu* Overexpressing Human Breast Cancer Xenografts," *Cancer Research*, 58:2825-2831.

Batra et al., (1993), "Insertion of Constant Region Domains of Human IgG1 into CD4-PE40 Increases Its Plasma Half-Life," *Mol. Immunol.*, 30:379-386.

Becker et al., (1996), "An Antibody-Interleukin 2 Fusion Protein Overcomes Tumor Heterogeneity by Induction of a Cellular Immune Response," *Proc. Natl. Acad. Sci.*, 93:7826-7831.

Becker et al., (1996), "Eradication of human hepatic and pulmonary melanoma metastases in SCID mice by antibody-interleukin 2 fusion proteins," *Proc. Natl. Acad. Sci. USA*, 93:2702-2707.

Beutler et al., (1988), "Tumor Necrosis, Cachexia, Shock, and Inflammation: A Common Mediator," *Ann. Rev. Biochem.*, 57:505-518.

Bissery et al., (1997), "The Taxoids," in *Cancer Therapeutics: Experimental and Clinical Agents*, Teicher, ed., 175-193.

Bjorn et al., (1985), "Evaluation of Monoclonal Antibodies for the Development of Breast Cancer Immunotoxins," *Cancer Research*, 45:1214-1221.

Boehm et al., (1997), "Antiangiogenic therapy of experimental cancer does not induce acquired drug resistance," *Nature*, 390:404-407.

Boehm et al., (1998), "Zinc-Binding of Endostatin Is Essential for Its Antiangiogenic Activity," *Biochemical and Biophysical Research Communications*, 252:190-194.

Boissel et al., (1993), "Erythropoietin Structure-Function Relationships," *The Journal of Biological Chemistry*, 268:15983-15993.

Brooks et al., (1994), "Integrin $\alpha_v\beta_3$ Antagonists Promote Tumor Regression by Inducing Apoptosis of Angiogenic Blood Vessels," *Cell*, 79:1157-1164.

Buchli et al., (1993), "Structural and Biologic Properties of a Human Aspartic Acid-126 Interleukin-2 Analog," *Archives of Biochemistry and Biophysics*, 307:2:411-415.

Burgess et al., (1990), "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, 111:2129-2138.

Canfield et al., (1991), "The Binding Affinity of Human IgG for its High Affinity Fc Receptor is Determined by Multiple Amino Acids in the CH2 Domain and Is Modulated by the Hinge Region," *Journal of Experimental Medicine*, 173:6:1483-1491.

Cao et al., (1996), "Kringle Domains of Human Angiostatin," *The Journal of Biological Chemistry*, 271:46:2946-29467.

Cao et al., (1997), "Kringle 5 of Plasminogen is a Novel Inhibitor of Endothelial Cell Growth," *The Journal of Biological Chemistry*, 272:36:22924-22928.

Capon et al., (1989), "Designing CD4 immunoadhesins for AIDS therapy," *Nature*, 337:525-531.

Caton et al., (1986), "Structural and functional implications of a restricted antibody response to a defined antigenic region on the influenza virus hemagglutinin," *The Embo Journal*, 5:7:1577-1587.

Chan et al., (1991), "Induction of Interferon γ Production by Natural Killer Cell Stimulatory Factor: Characterization of the Responder Cells and Synergy with Other Inducers," *J. Exp. Med.*, pp. 869-879.

Chang et al., (1989), "Overview of Interleukin-2 as an Immunotherapeutic Agent," *Seminars in Surgical Oncology*, 5:385-390.

Chang et al., (1996), "A Point Mutation in Interleukin-2 that Alters Ligand Internalization," *Journal of Biological Chemistry*, 271:23:13349-13355.

Chaudhary et al., (1988), "Selective killing of HIV-infected cells by recombinant human CD4-Pseudomonas exotoxin hybrid protein," *Nature*, 335:370-372.

Chaudhary et al., (1989), "A recombinant immunotoxin consisting of two antibody variable domains fused to Pseudomonas exotoxin," *Nature*, 339:394-397.

Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," *Journal of Immunology*, 159:1:351-358.

Cheon et al., (1994), "High-affinity binding sites for related fibroblast growth factor ligands reside within different receptor immunoglobulin-like domains," *Proc. Natl. Acad. Sci. USA*, 91:989-993.

Chuang et al., (1993), "Effect of new investigational drug taxol on oncolytic activity and stimulation of human lymphocytes," *Gynecol. Oncol.*, 49:291-298.

Cohen, S. L. et al., (1996), "Human leptin characterization," *Nature*, 382:589.

Cole et al., (1997), "Human IgG2 Variants of Chimeric Anti-CD3 Are Nonmitogenic to T Cells," *Journal of Immunology*, 159:3613-3621.

Collins et al., (1988), "Identification of Specific Residues of Human Interleukin 2 that Affect Binding to the 70-kDa Subunit (p70) of the Interleukin 2 Receptor," *Proc. Natl. Acad. Sci*, 85:7709-7713.

Colombo et al., (1996), "Amount of Interleukin 12 Available at the Tumor Site is Critical for Tumor Regression," *Cancer Research*, 56:2531-2534.

D'Amato et al., (1994), "Thalidomide is an inhibitor of angiogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Ding et al., (1988), "Zinc-Dependent Dimers Observed in Crystals of Human Endostatin," *Proceedings of the National Academy of Sciences of USA*, 95:10443-10448.

Earnest et al., (1992), "Piroxicam and Other Cyclooxygenase Inhibitors: Potential for Cancer Chemoprevention," *J. Cell. Biochem, Supp*, 161:156-166.

Eisenthal, (1990), "Indomethacin up-regulated the generation of lymphokine-activated killer-cell activity and antibody-dependent cellular cytotoxicity mediated by interleukin-2," *Cancer Immunol. Immunotherap.* 31:342-348.

Fell et al., (1991), "Genetic Construction and Characterization of Fusion Protein Consisting of a Chimeric F(ab') with Specificity for Carcinomas and Human IL-2," *The J. of Immunology*, 146:7:2446-2452.

Fell et al., (1992), "Chimeric L6 antitumor antibody," *The J. of Biol. Chem.*, 267:15552-15558.

Friedman, J. M. et al., (1998), "Leptin and the regulation of body weight in mammals," *Nature*, 395:763:770.

Gasson et al., (1984), "Purified Human Granulocyte Macrophage Colony-Stimulating Factor: Direct Action on Neutrophils," *Science*, 226:1339-1342.

Gately et al., (1998), "The Interleukin-12/Interleukin-12 Receptor system: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist," *Eur. J. Immunol.*, 25:200-206.

Gillies et al., (1989), "Expression of Human Anti-Tetanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen binding and biological activities of engineered mutant chimeric antibodies with human tumor specificities," *Hum. Antibod. Hybridomas*, 1:1:47-54.

Gillies et al., (1992), "Antibody-Targeted Interleukin 2 Stimulates T-Cell Killing of Autologous Tumor Cells," *Proc. Natl. Acad. Science*, 89:1428-1432.

Gillies et al., (1993), "Biological Activity and In Vivo Clearance of Antitumor Antibody/Cytokine Fusion Proteins," *Bioconjugate Chem.*, 4:230-235.

Gillies et al., (1998), "Antibody-IL-12 fusion proteins are effective in SCID mouse models of prostate and colon carcinoma matastases," *J. Immunology*, 160:2:6195-6203.

Gillis et al., (1978), "T Cell Growth Factor: Parameters of Production And A Quantitative Microassay for Activity," *Journal of Immunology*, 120:6:2027-2032.

Goeddel et al., (1986), "Tumor Necrosis Factors: Gene Structure and Biological Activities," *Pharm. Sciences*, pp. 597-609.

Gren et al., (1983), "A New Type of Leukocytic Interferon," *Dokl. Biochem.*, 269:91-95.

Griffon-Etienne et al., (1999), "Taxane-induced apoptosis decompresses blood vessels and lowers interstitial fluid pressure in solid tumors: clinical implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73:8:2081-2805.

Guyre et al., (1997), "Increased potency of Fc-receptor-targeted antigens," *Cancer Immunol. Immunother.*, 45:146-148.

Harris et al., (1993), "Therapeutic Antibodies—the Coming of Age," *Tibtech*, 11:42-44.

Harvill et al., (1995), "An IgG3-IL2 Fusion Protein Activates Complement, Binds FcYRI, Generates LAK Activity and Shows Enhanced Binding to the High Affinity IL-2R," *Immunotech.*, 1:95-105.

Harvill et al., (1996), "In vivo properties of an IgG3-IL-2 fusion protein: A general strategy for immune potentiation," *Journal of Immunology*, 157:7:3165-3170.

Hazama et al., (1993), "Adjuvant-Independent Enhanced Immune Responses to Recombinant Herpes Simplex Virus Type 1 Glycoprotein D by Fusion with Biologically Active Interleukin-2," *Vaccine*, 11:6:629-636.

He et al., (1998), "Humanization and Pharmacokinetics of Monoclonal Antibody with Specificity for Both E- and P-Selectin," *J. Immunol.*, 1029-1035.

Heijnen et al., (1996), "Antigen Targeting to Myeloid-specific Human FcYRI/CD64 Triggers Enhanced Antibody Responses in Transgenic Mice," *J. Clin. Invest.*, 97:2:331-338.

Heinzel et al., (1997), "In Vivo Production and Function of IL-12 p40 Homodimers," *J. Immunol.*, 158:4381-4388.

Hellstrom et al., (1986), "Antitumor effects of L6, an IgG2a antibody that reacts with most human carcinomas," *Proc. Natl. Acad. Sci.*, 83:18: 7059-7063.

Henkart, (1985), "Mechanism of Lymphocyte-Mediated Cytotoxicity," *Ann. Rev. Immunol.*, 3:31-58.

Herrmann et al., (1989), "Hematopoeitic Responses With Advanced Malignancy Treated With Recombinant Human Granulocyte-Macrophage Colony-Stimulating Factor," *Journal of Clinical Oncology*, 7:2:159-167.

Hohenester et al., (1998), "Crystal Structure of the Angiogenesis Inhibitor Endostatin at 1.5 Å Resolution," *EMBO Journal*, 17:6:1656-1664.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675.

Holden et al., (2001), "Augmentation of Antitumor activity of an Antibody-Interleukin 2 lmmunocytokine with Chemotherapeutic Agents," *Clinical Cancer Research*, 7:2862-2869.

Hoogenboom et al., (1991), "Construction and expression of antibody-tumor necrosis factor fusion proteins," *Molecular Immunology*, 28:9:1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096:4:345-354 (Abstract).

Hornick et al, (1999), "Pretreatment with a monoclonal antibody/interleukin-2 fusion protein direceted against DNA enhances the delivery of therapeutic molecules to solid tumors," *Clin. Cancer Res.*, 5:51-60.

Hu et al., (1996), "A Chimeric Lym-1/Interleukin 2 Fusion Protein for Increasing Tumor Vascular Permeability and Enhancing Antibody Uptake," *Cancer Research*, 56:4998-5004.

Huck et al., (1986), "Sequence of a human immunoglobulin gamma 3 heavy chain constant region gene: comparison with the other human Cγ genes," *Nucleic Acids Research*, vol. 14:4:1779-1789.

Huse et al., (1989), "Generation of a Large Combinatorial Library of the Immunoglobulin Repertoire in Phage Lambda," *Science*, 246:1275-1281.

Ilngber et al., (1990), "Synthetic analogues of fumagillin that inhibit angiogenesis and suppress tumour growth," *Nature*, 348:555-557.

Jones et al., (1986), "Replacing the complementarity-determining regions in a human antibody with those from a mouse," *Nature*, 321:6069:522-525.

Ju et al., (1987), "Structure-Function Analysis of Human Interleukin-2," *Journal of Biological Chemistry*, 262:12:5723-5731.

Jung et al., (1986), "Activation of human peripheral blood mononuclear cells by anti-T3: Killing of tumor target cells coated with anti-target-anti-T3 conjugates," *Proc. Natl. Acad. Sci.*, 83:4479-4483.

Junghans et al., (1996), "The protection receptor of IgG catabolism is the B2-micorgobulin-containing neonatal intestinal transport receptor," *Proc. Natl. Acad. Sci.*, 93:11:5512-5516.

Kang et al., (1991), "Antibody redesign by chain shuffling from random combinatorial immunoglobulin libraries," *Proc. Natl. Acad. Sci.*, 88:11120-11123.

Kappel et al., (1992), "Regulating gene expression in transgenic animals," *Current Opinion in Biotechnology* 3:548-553.

Karpovsky et al., (1984), "Production of Target-Specific Effector Cells using Hetero-Cross Linked Aggregate Containing Anti-Target Cell and AntiFcλ Receptor Antibodies," *Journal of Experimental Medicine*, 160:6:1686-1701.

Kim et al., (1997), "An Ovalbumin-IL-12 fusion protein is more effective than ovalbumin plus free recombinant IL-12 in inducing a T helper cell type 1-dominated immune response and inhibiting antigen-specific IgE production," *Journal Immunology*, 158:9:4137-4144.

Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.

Kranz et al., (1984), "Attachment of an anti-receptor antibody to non-target cells renders them susceptible to lysis by a clone of cytotoxic T lymphocytes," *Proc. Natl. Acad. Sci.*, 81:7922-7926.

Kuo et al., (2001), "Oligomerization-dependent Regulation of Motility and Morphogenesis by the Collagen XVIII NC1/Endostatin Domain," *Journal of Cell Biology*, 152:6:1233-1246.

LaVallie et al., (1993), "Cloning and Functional Expression of a cDNA Encoding the Catalytic Subunit of Bovine Enterokinase," *Journal of Biological Chemistry*, 268:31:23311-23317.

Lazar et al., (1988), "Transforming Growth Factor α: Mutation of Aspartic Acid 47 and Leucine 48 Results in Different Biological Activities," *Molecular and Cellular Biology*, 8:3:1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lieschke, et al., (1997), "Bioactive murine and human interleukin-12 fusion proteins which retain antitumor activity in vivo," *Nature Biotechnology*, 15:1:35-40.

Linsley et al., (1991), "CTLA-4 is a Second Receptor for B Cell Activation Antigen B7," *Journal of Experimental Medicine*, 174:3:561-569.

Liu et al., (1985), "Heteroantibody Duplexes Target Cells for Lysis by Cytotoxic T Lymphocytes," *Proc. Natl. Acad. Sci.*, 82:8648-8652.

Liu et al., (1988), "Hormone Conjugated with Antibody to CD3 Mediates Cytotoxic T Cell Lysis of Human Melanoma Cells," *Science*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92:10:3730-3736.

Lo et al., (1998), "High Level Expression and Secretion of Fc-X Fusion Proteins in Mammalian Cells," *Protein Engineering*, 11:6:495-500.

Lode et al., (1998), "Immunocytokines: a promising approach to cancer immunotherapy," *Pharmacol. Thera.*, 80:3:277-292.

Lode et al., (1998), "Natural Killer Cell-Mediated Eradication of Neuroblastoma Metastases to Bone Marrow by Targeted Interleukin-2 Therapy," *Blood*, 91:5:1706-1715.

Lode et al., (1999), "Synergy between an antiangiogenic integrin $\alpha_v$ antagonist and an antibody-cytokine fusion protein eradicates spontaneous tumor metastases," *Proc. Natl. Acad. Sci.*, 96:1591-1596.

Lode et al., (1999), "Tumor-targeted IL-2 amplifies T cell-mediated immune response induced by gene therapy with single-chain IL-12," *Proc. Natl. Acad. Sci.*, 96:8591-8596.

Lode et al., (2000), "Amplification of T Cell Mediated Immune Responses by Antibody-Cytokine Fusion Proteins," *Immunological Investigations*, 29:2:117-120.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84:8:2457-2466.

Mark et al., (1992), "Expression and characterization of hepatocyte growth factor receptor-IgG fusion proteins," *Journal of Biological Chemistry*, 267:36:26166-26171.

Martinotti et al., (1995), "CD4 T Cells Inhibit in vivo the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse IgG1," *J. Immunology*, 158:5:2211-2217.

Mestre et al., (1997), "Retinoids Suppress Epidermal Growth Factor-induced Transcription of Cyclooxygenase-2 in Human Oral Squamous Carcinoma Cells," *Cancer Research*, 57:2890-2895.

Mosmann et al., (1989), "TH1 and TH2 Cells: Different Patterns of Lymphokine Secretion Lead to Different Functional Properties," *Ann. Rev. Immunol.*, 7:145-173.

Mott et al., (1995), "The Solution Structure of the F42A Mutant of Human Interleukin 2," *J. Mol. Biol.*, 247:979-994.

Mullins et al., (1998), "Interleukin-12 overcomes paclitaxel-mediated suppression of T-cell proliferation," *Immunopharmacol. Immunotoxicol.*, 20:4:473-492.

Murphy et al., (1986), "Genetic construction, expression, and melanoma-selective cytotoxicity of a diphtheria toxin-related α-melanocyte-stimulating hormone fusion protein," *Proc. Natl. Acad. Sci.*, 83:8258-8262.

Murphy, (1988), "Diphtheria-related peptide hormone gene fusions: A molecular gene approach to chimeric toxin development," *Immunotoxins*, 123-140.

Nedwin et al., (1985), "Human Lymphotoxin and Tumor Necrosis Factor Genes: Structure, Homology and Chromosomal Localization," *Nucleic Acids Research*, 13:17:6361-6373.

Netti et al., (1995), "Time-dependent behavior of interstitial fluid pressure in solid tumors: implications for drug delivery," *Cancer Research*, 55:5451-5458.

Netti et al., (1999), "Enhancement of fluid filtration across tumor vessels: implication for delivery of macromolecules," *Proc. Nat. Acad. Sci*, 96:3137-3142.

Neuberger et al., (1984), "Recombinant Antibodies Possessing Novel Effector Functions," *Nature*, 312:604-608.

O'Reilly et al., (1994), "Angiostatin: A Novel Angiogenesis Inhibitor That Mediates the Suppression of Metastases by a Lewis Lung Carcinoma," *Cell*, 79:315-328.

O'Reilly et al., (1996), "Angiostatin induces and sustains dormancy of human primary tumors in mice," *Nature Medicine*, 2:6:689-692.

O'Reilly et al., (1997), "Endostatin: An Endogenous Inhibitor of Angiogenesis and Tumor Growth," *Cell*, 88:277-285.

Pastan et al., (1989), "Pseudomonas Exotoxin: Chimeric Toxins," *Journal of Biological Chemistry*, 264:26:15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target cell antibodies," *J. Exp. Medicine*, 163:166-178.

Perez et al., (1989), "Isolation and Characterization of a cDNA Encoding the KS1/4 Epithelial Carcinoma Marker," *Journal of Immunology*, 142:10:3662-3667.

Polizzi et al., (1999), "A novel taxane with improved tolerability and therapeutic activity in a panel of human tumor xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Nat'l Acad. Sci.*, 94:20:10889-10894.

Reisfeld et al., (1996), "Recombinant antibody fusion proteins for cancer immunotherapy," *Current Topics in Microbiology and Immunology*, 27-53.

Reisfeld et al., (1997), "Immunocytokines: a new approach to immunotherapy of melanoma," *Melanoma Research*, 7:2:S99-S106.

Riethmuller et al., (1994), "Randomised trial of monoclonal antibody for adjuvant therapy of resected Dukes' C colorectal carcinoma," *The Lancet*, 343:1177-1183.

Roessler et al., (1994), "Cooperative interactions between the interleukin 2 receptor α and β chains alter the interleukin 2-binding affinity of the receptor subunits," *Proc. Natl. Acad. Sci.*, 91:3344-3347.

Roitt et al., (1993), "The Role of $T_H$ Cells in the Selection of Effector Mechanisms Directed Against Target Antigens," *Immunology*, Third Edition, 8.3-8.4.

Rosenberg, (1988), "Immunotherapy of Cancer Using Interleukin 2: current status and future prospects," *Immunology Today*, 9:2:58-62.

Rozwarski et al., (1994), "Structural comparisons among the short-chain helical cytokines," *Structure*, 2:3:159-173.

Santon et al., (1986), "Effects of Epidermal Growth Factor Receptor Concentration on Tumorigenicity of A431 Cells in Nude Mice," *Cancer Research*, 46:4701-4705.

Sasaki et al., (1998), "Structure, function and tissue forms of the C-terminal globular domain of collagen XVII containing the angiogenesis inhibitor endostatin," *The EMBO Journal*, 17:15:4249-4256.

Sauve et al., (1991), "Localization in human interleukin 2 of the binding site of the α chain (p55) of the interleukin 2 receptor," *Proc. Natl. Acad. Sci.*, 88:4636-4640.

Schnee et al., (1987), "Construction and expression of a recombinant antibody-targeted plasminogen activator," *Proc. Natl. Acad. Sci.*, 84:6904-6908.

Schoenhaut et al., (1992), "Cloning and Expression of Murine IL-12," *Journal of Immunology*, 148:11:3433-3340.

Senter et al., (1988), "Anti-tumor effects of antibody-alkaline phosphatase conjugates in combination with etoposide phosphate," *Proc. Natl. Acad. Sci.*, 85:13:4842-4846.

Shanafelt et al., (2000), "A T-cell-selective interleukin 2 mutein exhibits potent antitumor activity and is well tolerated in vivo," *Nature Biotechnology*, 18:1197-1202.

Sharma et al., (1999), "T cell-derived IL-10 promotes lung cancer growth by suppressing both T cell and APC function," *Journal of Immunology*, 163:5020-5028.

Shen et al., (1986), "Heteroantibody-Mediated Cytotoxicity: Antibody to the high affinity Fc receptor for IgG mediates cytotoxicity by human monocytes that is enhanced by interferon-λ and is not blocked by human IgG," *Journal of Immunology*, 137:11:3378-3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et al., (1990), "Expression and characterization of an antibody binding specificity joined to insulin-like growth factor 1: Potential applications for cellular targeting," *Proc. Natl. Acad. Sci.*, 87:5322-5326.

Sim et al., (1997), "A Recombinant Human Angiostatin Protein Inhibits Experimental Primary and Metastatic Cancer," *Cancer Research*, 57:1329-1334.

Stevenson et al., (1997), "Conjugation of Human Fcγ in Closed-Hinge or Open-Hinge Configuration to Fab'γ and Analogous Ligands," *Journal of Immunology*, 158:2242-2250.

Sulitzeanu et al., (1993), "Immunosuppressive factors in human cancer," *Adv. Cancer Research*, 60:247-267.

Taniguchi et al., (1983), "Structure and expression of a cloned cDNA for human interleukin-2," *Nature*, 302:305-309.

Tao et al., (1989), "Studies of Aglycosylated Chimeric Mouse IgG: Role of Carbohydrate in the Structure and Effector Functions Mediated by the Human IgG Constant Region," *Journal of Immunology*, 143:8:2595-2601.

Tao et al., (1993), "Structural Features of Human Immunoglobulin G that Determine Isotype-Differences in Complement Activation," *Journal of Experimental Medicine*, 178:2:661-667.

Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 990-993, 1278-1283 ($17^{th}$ ed. 1999).

Till et al., (1988), "An Assay that Predicts the Ability of Monoclonal Antibodies to Form Potent Ricin A Chain-containing Immunotoxins," *Cancer Research*, 48:5:1119-1123.

Till et al., (1988), "HIV-Infected Cells are Killed by rCD4-Ricin A Chain," *Science*, 242:1166-1168.

Trinchieri, (1994), "Interleukin-12: A Cytokine Produced by Antigen-Presenting Cells With Immunoregulatory Functions in the Generation of T-Helper Cells Type 1 and Cytotoxic Lymphocytes," *Blood*, 84:4008-4027.

Vagliani et al., (1996), "Interleukin 12 Potentiates the Curative Effect of a Vaccine Based on Interleukin 2-transduced Tumor Cells," *Cancer Research*, 56:467-470.

Varki et al., (1984), "Antigens Associated with a human lung adenocarcinoma defined by monoclonal antibodies," *Cancer Research*, 44:681-687.

Verhoeyen et al., (1988), "Reshaping Human Antibodies: Grafting an Antilysozyme Activity," *Science*, 239:1534-1536.

Villunger et al., (1997), "Constitutive expression of Fas (Apo-1/CD95) ligand on multiple myeloma cells: a potential mechanism of tumor-induced suppression of immune surveillance," *Blood*, 90:1:12-20.

Watanabe et al., (1997), "Long-term depletion of naive T cells in patients treated for Hodgkin's disease," *Blood*, 90:9:3662-3672.

Wen et al., (1993), "Erythropoietin Structure-Function Relationships: High Degree of Sequence Homology Among Mammals," *Blood*, 82:1507-1516.

Williams et al., (1986), "Production of antibody-tagged enzymes by myeloma cells: application to DNA polymerase I Klenow fragment," *Gene*, 43:319-324.

Williams et al., (1987), "Diphtheria toxin receptor binding domain substitution with interleukin-2: genetic construction and properties of a diphtheria toxin-related interleukin-2 fusion protein," *Protein Engineering*, 1:6:493-498.

Wooley et al., (1993), "Influence of a Recombinant Human Soluble Tumor Necrosis Factor Receptor Fc Fusion Protein on Type II Collagen-Induced Arthritis in Mice," *Journal Immunology*, 151: 6602-6607.

Wu et al., (1997), "Suppression of Tumor Growth with Recombinant Murine Angiostatin," *Biochemical and Biophysical Research Communications*, 236:651-654.

Xiang et al., (1997), "Elimination of Established Murine Colon Carcinoma Metastases by Antibody-Interleukin 2 Fusion Protein Therapy," *Cancer Research*, 57:4948-4955.

Zheng et al., (1995), "Administration of noncytolytic IL-10/Fc in muring models of lipopolysaccharide-induced septic shock and allogenic islet transplantation," *Journal of Immunology*, 154:5590-5600.

Xu et al., (1994), "Residue at Position 331 in the IgG1 and IgG4 CH2 Domains Contributes to Their Differential Ability to Bind and Activate Complement," *J. Biol. Chem.*, 269:3469-3474.

Angal et al., (1993), "A Single Amino Acid Substitution Abolishes the Heterogeneity of Chimeric Mouse/Human (IgG4) Antibody," *Molecular Immunology*, 30:105-108.

Batova et al., (1999), "The Ch 14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263.

Becker et al., (1996), "Long-lived and transferable tumor immunity in mice after targeted interleukin-2 therapy," *J Clin Invest.*, 98(12):2801-4.

Becker et al., (1996), "T Cell-mediated eradication of murine metastatic melanoma induced by targeted interleukin 2 therapy," *J Exp Med.*, 183(50):2361-6.

Bitonti et al., (2002), "Transepithelial Absorption of an Erythropoietin-Fc Fusion Protein After Delivery to the Central Airways," *Respiratory Drug Delivery*, 8:309-312.

Briggs et al., (1974), "Hepatic Clearance of Intact and desialylated Erythropoietin," *American Journal of Physiology*, 227:1385-1388.

Chuang et al., (1994), "Alteration of Lymphocyte Microtubule Assembly, Cytotoxicity, and Activation by the Anticancer Drug Taxol," *Cancer Research*, 54:1286-1291.

Cruse et al., (1995), Illustrated Dictionary of Immunology, CRC Press, NY, p. 156-7.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: amplification of anti-cancer immunity," *Cancer Immunol Immunother*52:297-308.

Dolman et al., (1998), "Suppression of human prostate carcinoma metastases in severe combined immunodeficient mice by interleukin 2 immunocytokine therapy," *Clin Cancer Res.*, 4(10):2551-7.

Duncan et al., (1988), "The binding site for C1q on IgG," *Nature*, 332:738-740.

Egrie et al., (2001), "Development and characterization of novel erythropoiesis stimulating protein (NESP)," *Nephrol. Dial. Transplant.*, 16:3-13.

Elliott et al., (1997), "Mapping of the Active Site of Recombinant Human Erythropoietin," *Blood*, 89(2):493-502.

Fell et al., (1991), "Genetic Construction and Characterization of Fusion Protein Consisting of a Chimeric F(ab') with Specificity for Carcinomas and Human IL-2," *The J. of Immunology*, 146:7:2446-2452.

Fibi et al., (1995), "N- and O-Glycosylation Muteins of Recombinant Human Erythropoietin Secreted From BHK-21 Cells," *Blood*, 85:1229-1236.

Frost et al., (1997), "A Phase I/IB Trial of Murine Monoclonal Anti-GD2 Antibody 14.G2a plus Interlukin-2 Children with Refractory Neuroblastoma", *Cancer*, 80:317-33.

Gan et al., (1999), "Specific enzyme-linked immunosorbent assays for quantitation of antibody-cytokine fusion proteins," *Clin Diagn Lab Immunol.*, 6(2):236-42.

Gillies et al., (1991), "Expression of genetically engineered immunoconjugates of lymphotoxin and a chimeric anti-ganglioside GD2 antibody," *Hybridoma.*, 10(3):347-56.

Gillies et al., (1999), "Improving the Efficacy of Antibody-Interleukin 2 Fusion Proteins by Reducing Their Interaction with Fc Receptors," *Cancer Research*, 59:2159-2166.

Gillies et al., (2002), "Bi-functional cytokine fusion proteins for gene therapy and antibody-targeted treatment of cancer," *Cancer Immunol Immunother.*, 51(8):449-60.

Gillies et al., (2002), "Improved circulating half-life and efficacy of an antibody-interleukin 2 immunocytokine based on reduced intracellular proteolysis," *Clin. Cancer Res.*, 8(1):210-6.

Greene et al., (1975), "Neuronal properties of hybrid neuroblastoma X sympathetic ganglion cells", *Proc. Natl. Acad. Sci. USA*, 72:4923-4927.

Hammerling et al., (1996), "In vitro bioassay for human erythropoietin based on proliferative stimulation of an erythroid cell line and analysis of carbohydrate-dependent microheterogeneity," *Journal of Pharmaceutical and Biomedical Analysis*, 14:1455-1469.

Hank et al., (2003), "Determination of peak serum levels and immune response to the humanized anti-ganglioside antibody-interleukin-2 immunocytokine," *Methods Mol Med.*, 85:123-31.

Haraguchi, (1994), Isolation of GD3 synthase gene by expression cloning of GM3 α-2,8-sialyltransferase cDNA using anti-GD2 monoclonal antibody, *Proc. Natl. Acad. Sci. USA.*, 91(22):10455-9.

Harris, (1995), "Processing of C-terminal lysine and arginine residues of proteins isolated from mammalian cell culture," *J. Chromatogr. A.*, 705:129-134.

Hezareh et al, (2001), "Effector function activities of a panel of mutants of a broadly neutralizing antibody against human immunodeficiency virus type 1," *J. Virol.*, 75(24):12161-8.

Idusogie et al., (2000), "Mapping of the C1q binding site on rituxan, a chimeric antibody with a human IgG1 Fc," *J. Immunol.*, 164(8):4178-84.

Imboden et al., (2001), "The level of MHC class I expression on murine adenocarcinoma can change the antitumor effector mechanism of immunocytokinetherapy," *Cancer Res.*, 61(4):1500-7.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26:126-131.

Kendra et al., (1999), "Pharmacokinetics and Stability of the ch 14.18-Interleukin-2 Fusion Protein in Mice," *Cancer Immunol. Immunotherapy*, 48:219-229.

King et al., (2003), "A Phase I/IB clinical trial of the immunocytokine hu14.18-IL2 (EMD 273063) in patients with melanoma," Author's manuscript dated Jun. 6, 2003.

Kitamura et al., (1989), "Establishment and Characterization of a Unique Human Cell Line that Proliferates Dependently on GM-CSF, IL-3, or Erythropoietin," *Journal of Cellular Physiology*, 140:323-334.

Kushner et al., (2001),"Phase II Trial of the Anti-GD2 Monoclonal Antibody 3F8 and Granulocyte-Macrophage Colony-Stimulating Factor for Neuroblastoma", *J. Clin. Oncol.*, 19:4189-94.

Locatelli et al., (2001), "Darbepoetin alfa Amgen," *Current Opinion in Investigational Drugs*, 2:1097-1104.

Lode et al., (1997), "Targeted interleukin-2 therapy for spontaneous neuroblastoma metastases to bone marrow," *J Natl Cancer Inst.*, 89(21):1586-94.

Lode et al., (2000), "What to do with targeted IL-2," *Drugs Today*, 36(5):321-36.

Lode et al., (2000), "Melanoma immunotherapy by targeted Il-2 depends on CD4(+) T-cell help mediated by CD40/CD40L interaction," *J. Clin. Invest.*, 105(11):1623-30.

Macdougall, (2002), "Optimizing the Use of Erythropoietic Agents—Pharmacokinetic and Pharmacodynamic Considerations," *Nephrol. Dial. Transplant.*, 17:66-70.

Metelitsa et al., (2002), "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis," *Blood*, 99(11):4166-73.

Mueller et al., (1997), "Humanized porcine VCAM-specific monoclonal antibodies with chimeric IgG2/G4 constant regions block human leukocyte binding to porcine endothelial cells," *Molecular Immunology*, 34(6):441-452.

Mullins et al., (1997), "Taxol-mediated changes in fibrosarcoma-induced immune ell function: modulation of antitumor activities," *Cancer Immunol Immunother*, 45:20-28.

Naramura et al., "Mechanisms of cellular cytotoxicity mediated by a recombinant antibody-IL2 fusion protein against human melanoma cells," *Immunol Lett.*, 39(1):91-9, (1994).

Neal et al., (2003), "NXS2 murine neuroblastomas express increased levels of MHC class I antigens upon recurrence following NK-dependent immunotherapy," *Cancer Immunol Immunother.*, Pub. Med ID: 14504825.

Ngo et al., (1994), "Computational Complexity, Protein Structure Prediction, and the Levinthal Paradox" pp. 433-440 and 492-495.

Niethammer et al., (2001) "An oral DNA vaccine against human carcinoembryonic antigen (CEA) prevent growth and dissemination of Lewis Lung carcinoma in CEA transgenic mice," *Vaccine*, 20(3-4):421-9.

Niethammer et al., (2001) "Targeted Interleukin 2 therapy enhances protective immunity induced by an autologous murine melanoma," *Cancer Res.*, 61(16):6178-84.

Nimtz et al., (1993) Structures of Sialylated Oligosaccharides of Human Erythropoietin Expressed in recombinant BHK-21 Cells, *Eur. J. Biochem.*, 213:39-56.

Pancook et al., (1996), "Eradication of established hepatic human neuroblastoma metastases in mice with severe combined immunodeficiency by antibody-targeted interleukin-2," *Cancer Immunol Immunother.*, 42(2):88-92.

Park et al., (2000), "Efficiency of promoter and cell line in high-level expression of erythropoietin," *Biotechnol. Appl. Biochem.*, 32:167-172.

Reisfeld et al., (1996), "Antibody-interleukin 2 fusion proteins: a new approach to cancer therapy," *J Clin Lab Anal.*, 10(3):160-6.

Reisfeld et al., (1996), "Involvement of B lymphocytes in the growth inhibition of human pulmonary melanoma metastases in athymic nu/nu mice by an antibody-lymphotoxin fusion protein," *Cancer Res.*, 56(8):1707-12.

Ruehlmann et al., (2001), "MIG (CIXCL9) chemokine gene therapy combines with antibody-cytokine fusion protein to suppress growth and dissemination of murine colon carcinoma," *Cancer Res.*, 61(23):8498-503.

Sabzevari et al., (1994), "A recombinant antibody-interleukin 2 fusion protein suppresses growth of hepatic human severe combined immunodeficiency mice," *Proc Natl Acad Sci USA*, 91(20):9626-30.

Seidenfeld et al., (2001), "Epoietin Treatment of Anemia Associated with Cancer Therapy: A Systematic Review and Meta-analyis of controlled Clinical Trials," *Journal of National Cancer Institute*, 93:1204-1214.

Shinkawa et al., (2003), "The Absence of Fucose but Not the Presence of Galactose or Bisecting N-Acetylglucosamine of Human IgG1 Comples-type Oligosaccharides Shows the Critical Role of Enhancing Antibody-dependent Cellular Cytoxicity", *J. Biol. Chem.*, 278:3466-3473.

Spiekermann et al., (2002), "Receptor-mediated Immunoglobulin G Transport Across Mucosal Barriers in Adult Life: Functional Expression of FcRn in the Mammalian Lung," *J. Exp. Med.*, 196:303-310.

Strom et al., (1996), "Therapeutic Approach to Organ Transplantation", *Blackwell Science*, Chapter 36, pp. 451-456.

Syed et al., (1998), "Efficiency of signaling through cytokine receptors depends critically on receptor orientation," *Nature*, 395:511-516.

Thommesen et al., (2000), "Lysine 322 in the human IgG3 CH2 domain is crucial for antibody dependent complement activation", *Mol. Immunol.*, 37(16):995-1004.

Wells, (1990), "Additivity of Mutational Effect in Proteins," *Biochemistry*, 29(37):8509-8517.

Xiang et al., (1998), "Induction of persistent tumor-protective immunity in mice cured of established colon carcinoma metastases," *Cancer Res.*, 58(17)3918-25.

Xiang et al., (1999) "T Cell memory against colon carcinoma is long-lived in the absence of antigen," *J Immunol.*, 163(7):3676-83.

Xiang et al., (2001), "A dual function DNA vaccine encoding carcinoembryonic antigen and CD40 ligand trimer induces T cell-mediated protective immunity against colon cancer in carcinoembryonic antigen-transgenic mice," *J Immunol.*, 167(8):4560-5.

Xiang et al., (2001), "Protective immunity against human carcinoembryonic antigen (CEA) induced by an oral DNA vaccine in CEA-transgenic mice," *Clin Cancer Res.*, 7(3 Suppl):856s-864s.

Yu et al., (1998), "Phase I Trial of a Human-Mouse Chimeric Anti-Disialoganglioside Monoclonal Antibody ch14.8 in Patients With Refractory Neuroblastoma and Osteosarcoma", *J. Clin. Oncol.*, 16:2169-80.

Zagozdzon et al., (1999), "Potentiation of antitumor effect of IL-12 in combination with paclitaxel in murine melanoma model in vivo," *International Journal of Molecular Medicine*, 4:645-648.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Conner et al., (2004), "Ex vivo Evaluation of Anti-EpCAM Immunocytokine huKS-IL2 in Ovarian Cancer," *J. Immunotherapy*, 27:211-219.

de la Salle et al., (1996), "FcγR on Human Dendritic Cells," in *Human IgG Receptors*, pp. 39-55, van de Winkel et al. (eds.), R.G. Landes Co.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Elliott et al., (1996), "Fine-Structure Epitope Mapping of Antierythropoietin Monoclonal Antibodies Reveals a Model of Recombinant Human Erythropoietin Structure," *Blood*, 87(7):2702-2713.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Handgretinger et al., (1995), "A Phase I Study of Human/Mouse Chimeric Anti-ganglioside GD2 Antibody ch14.18 in Patients with Neuroblastoma," *European J. Cancer*, 31A(2):261-267.

Hank et al., (1996), "Activation of Human Effector Cells by a Tumor Reactive Recombinant Anti-ganglioside GD2 Interleukin-2 Fusion Protein (ch14.18-IL2)," *Clin Cancer Research*, 2(12):1951-1959.

Hurn et al., (1980), "Production of Reagent Antibodies," *Methods in Enzymology*, 70: 104-142.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Ko et al., (2004), "Safety, Pharmacokinetics, and Biological Pharmacodynamics of the Immunocytokine EMD 273066 (huKS-IL2)," *J. Immunotherapy*, 27:232-239.

Lo et al., (1992), "Expression and Secretion of an Assembled Tetrameric CH2-deleted Antibody in *E. coli.*," *Hum. Antibod. Hybridomas*, 3:123-128.

Maecker et al., (1997), "DNA Vaccination with Cytokine Fusion Constructs Biases the Immune Reponse to Ovalbumin," *Vaccine*, 15(15):1687-1696.

Mueller et al., (1990), "Enhancement of Antibody-Dependent Cytotoxicity With A Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA*, 87:5702-5705.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Pertl et al., (2003), "Immunotherapy with a Posttranscriptionally Modified DNA Vaccine Induces Complete Protection Against Metastatic Neuroblastoma," *Blood*, 101(2):649-654.

Reisfeld et al., (1994), "Potential of Genetically Engineered Anti-Ganglioside GD2 Antibodies for Cancer Immunotherapy," *Prog. Brain Res.*, 101:201-212.

Saleh et al., (1992), "Phase I Trial of the Chimeric Anti-GD2 Monoclonal Antibody ch14.18 in Patients With Malignant Melanoma," *Hum. Antiob. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, 179:1109-1118.

Schlom (1991), "Monoclonal Antibodies: They're More and Less Than You Think," in *Molecular Foundations of Oncology*, pp. 95-133.

Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Wen et al., (1994), "Erythropoietin Structure-Function Relationships: Identification of Functionally Important Domains," *J. Biological Chemistry*, 269(36):22839-22846.

Gurewich et al., (1988), "Characterization of the Intrinsic Fibrinolytic Properties of Pro-urokinase through a Study of Plasmin-resistant Mutant Forms Produced by Site-specific Mutagenesis of Lysine$^{158}$," J. Clin. Invest., 82:1956-1962.

Miyake et al., (1988), "Synthesis of Recombinant Human Single-Chain Urokinase-Type Plasminogen Activator Variants Resistant to Plasmin and Thrombin," *J. Biochem.*, 104:643-647.

Nelles et al., (1987), "Characterization of Recombinant Human Single Chain Urokinase-type Plasminogen Activator Mutants Produced by Site-specific Mutagenesis of Lysine$^{158}$," *The Journal of Biological Chemistry*, 262(12):5682-5689.

Aichele et al., (1994), "Peptide-Induced T-Cell Tolerance to Prevent Autoimmune Diabetes in a Transgenic Mouse Model," *Proc. Natl. Acad. Sci. USA*, 91:444-448.

Altschul et al., (1990), "Basic Local Alignment Search Tool," *J. Mol. Biol.*, 215:403-10.

Altschul et al., (1997), "Gapped BLAST and PSI-BLAST: A New Generation of Protein Database Search Programs," *Nucleic Acids Res.*, 25(17):3389-402.

Anderson et al., (1980), "Characterization of the Fc Receptor for IgG on a Human Macrophage Cell Line U937," *J. Immunol.*, 125:2735-41.

Anderson et al., (1994), "Effects of Route and Formulation on Clinical Pharmacokinetics of Interleukin-2," *Clin. Pharmacokinet.*, 27(1):19-31.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Barbulescu et al., (1998), "IL-12 and IL-18 Differentially Regulate the Transcriptional Activity of the Human IFN-$_\gamma$ Promoter in Primary CD4$_+$ T Lymphocytes," *J. Immunol.*, 160:3642-7.

Becker et al., (1996), "An Antibody-Interleukin 2 Fusion Protein Overcomes Tumor Heterogeneity by Induction of a Cellular Immune Response," *Proc. Natl. Acad. Sci. USA*, 93:7826-7831.

Bednarek et al., (1991), "Soluble HLA-A2.1 Restricted Peptides that are Recognized by Influenza Virus Specific Cytotoxic T Lymphocytes," *J. Immunol. Methods*, 139:41-47.

Benacerraf et al., (1959), "The Clearance of Antigen Antibody Complexes from the Blood by the Reticuloendothelial System," *J. Immunol.*, 82:131-7.

Bohm, (1994), "On the Use of LUDI to Search the Fine Chemicals Directory for Ligands of Proteins of Known Three-Dimensional Structure," *J. Comput. Aided Mol. Des.*, 8:623-32.

Bohm, (1994), "The Development of a Simple Empirical Scoring Function to Estimate the Binding Constant for a Protein-Ligand Complex of Known Three-Dimensional Structure," *J. Comput. Aided Mol. Des.*, 8:243-56.

Bohm, (1998), "Prediction of Binding Constants of Protein Ligands: A Fast Method for the Prioritization of Hits Obtained from De Novo Design or 3D Database Search Programs," *J. Comput. Aided Mol. Des.*, 12(4):309-23.

Boshart et al., (1985), "A Very Strong Enhancer is Located Upstream of an Immediate Early Gene of Human Cytomegalovirus," *Cell*, 41:521-530.

Boulianne et al., (1984), "Production of Functional Chimaeric Mouse/Human Antibody," *Nature*, 312:643-6.

Bourgois et al., (1974), "Determination of the Primary Structure of a Mouse IgG2a Immunoglobulin Amino Acid Sequence of the Fc Fragment: Implications for the Evolution of Immunoglobulin Structure and Function," *Eur. J. Biochem.*, 43:423-35.

Brambell et al., (1964), "A Theoretical Model of Gamma-Globulin Catabolism," *Nature*, 203:1352-54.

Brazolot Millan et al., (1998), "Cpg DNA Can Induce Strong TH1 Humoral and Cell-Mediated Immune Responses against Hepatitis B Surface Antigen in Young Mice," *Proc. Natl. Acad. Sci. USA*, 95:15553-8.

Brekke et al., (1994), "Human IgG Isotype-Specific Amino Acid Residues Affecting Complement-Mediated Cell Lysis and Phagocytosis," *Eur. J. Immunol.*, 24:2542-2547.

Brem et al., (1993), "The Combination of Antiangiogenic Agents to Inhibit Primary Tumor Growth and Metastasis," *J. Pediatr. Surg.*, 28:1253-7.

Brocklebank et al., (2001), "Enumeration of CD34+ Cells in Cord Blood: A Variation on a Single-Platform Flow Cytometric Method Based on the ISHAGE Gating Strategy," *Cytometry*,46(4):254-61.

Brooks et al., (1983), "CHARMM: A Program for Macromolecular Energy Minimization and Dynamics Calculations," *J. Comput. Chemistry*, 4:187-217.

Broudy et al., (1988), "Recombinant Human Erythropoietin: Purification and Analysis of Carbohydrate Linkage," *Arch. Biochem. Biophys.*, 265:329-36.

Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Bumol et al., (1982), "Unique Glycoprotein-Proteoglycan Complex Defined by Monoclonal Antibody on Human Melanoma Cells," *Proc. Natl. Acad. Sci. USA*, 79:1245-9.

Carnemolla et al., (1989), "A Tumor-Associated Fibronectin Isoform Generated by Alternative Splicing of Messenger RNA Precursors," *J. Cell. Biol.*, 108:1139-1148.

Carnemolla et al., (1992), "The Inclusion of the Type III Repeat ED-B in the Fibronectin Molecule Generates Conformational Modifications that Unmask a Cryptic Sequence," *J. Biol. Chem.*, 267(34):24689-24692.

Cazzola et al., (1998), "Red Blood Cell Precursor Mass as an Independent Determinant of Serum Erythropoietin Level," *Blood*, 91:2139-45.

Chan et al., (1992), "Mechanisms of IFN-Gamma Induction by Natural Killer Cell Stimulatory Factor (NKSF/IL-12). Role of Transcription and mRNA Stability in the Synergistic Interaction Between NKSF and IL-2," *J. Immunol.*, 148:92-98.

Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Cheetham, (1998), "NMR Structure of Human Erythropoietin and a Comparison with its Receptor Bound Conformation," *Nat. Struct. Biol.*, 5:861-6.

Ciardiello et al., (1996), "Antitumor Activity of Combined Blockade of Epidermal Growth Factor Receptor and Protein Kinase A," *J. Natl. Cancer Inst.*, 88:1770-6.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Congote et al., (1984), Abstract 364 in "Proceedings 7th Intl. Congress of Endocrinology," Quebec City, Quebec.

Congote, (1983), "Isolation of Two Biologically Active Peptides, Erythrotropin I and Erythrotropin II from Fetal Calf Intestine," *Biochem. Biophys. Res. Commun.*, 115(2):477-83.

Congote, (1984), "Extraction from Fetal Bovine Serum of Erythrotropin, an Erythroid Cell-Stimulating Factor," *Anal. Biochem.*, 140:428-33.

Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

Cunningham et al., (1989), "High-Resolution Epitope Mapping of Hgh-Receptor Interactions by Alanine-Scanning Mutagenesis," *Science*, 244:1081-85.

Curiel et al., (1991), "Adenovirus Enhancement of Transferrin-Polylysine-Mediated Gene Delivery," *Proc. Natl. Acad. Sci. USA*, 88:8850-4.

Dauber-Osguthorpe et al., (1988), "Structure and Energetics of Ligand Binding to Proteins: *Escherichia coli* Dihydrofolate Reductase-Trimethoprim, A Drug-Receptor System," *Proteins*, 4(1):31-47.

Daugherty et al., (1991), "Polymerase Chain Reaction Facilities the Cloning, CDR-Grafting, and Rapid Expression of a Murine Monoclonal Antibody Directed Against the CD18 Component of Leukocyte Integrins," *Nucleic Acid Res.*, 19:2471-2476.

De Bruijn et al., (1995), "Phagocyte-Induced Antigen-Specific Activation of Unprimed CD8+ T Cells in Vitro," *Eur. J. Immunol.*, 25:1274-85.

Delorme et al., (1992), "Role of Glycosylation on the Secretion and Biological Activity of Erythropoietin," *Biochemistry*, 31:9871-6.

Desai et al., (1992), "IL-12 Receptor. II. Distribution and Regulation of Receptor Expression," *J. Immunol.*, 148:3125-32.

Donnelly et al., (1993), "Targeted Delivery of Peptide Epitopes to Class I Major Histocompatibility Molecules by a Modified Pseudomonas Exotoxin," *Proc. Natl. Acad. Sci. USA*, 90:3530-4.

Donnelly et al., (1997), "DNA Vaccines," *Annu. Rev. Immunol.*, 15:617-48.

Dube et al., (1988), "Glycosylation at Specific Sites of Erythropoietin is Essential for Biosynthesis, Secretion, and Biological Function," *J. Biol. Chem.*, 263:17516-21.

Ellison et al., (1982), "The Nucleotide Sequence of a Human Immunoglobulin C Gamma1 Gene," *Nucleic Acids Res.*, 10:4071-9.

Faas et al., (1993), "Phenotypically Diverse Mouse Thymic Stromal Cell Lines which Induce Proliferation and Differentiation of Hematopoietic Cells," *Eur. J. Immunol.*, 23:1201-14.

Farner et al., (1995), "Distinction Between Gamma C Detection and Function in YT Lymphoid Cells and in the Granulocyte-Macrophage Colony-Stimulating Factor-Responsive Human Myeloid Cell Line, Tf-1," *Blood*, 86:4568-78.

Fawell et al., (1994), "Tat-Mediated Delivery of Heterologous Proteins into Cells," *Proc. Natl. Acad. Sci. USA*, 91:664-8.

Fu et al., (1993), "The Sheep Erythropoietin Gene: Molecular Cloning and Effect of Hemorrhage on Plasma Erythropoietin and Renal/Liver Messenger RNA in Adult Sheep," *Mol. Cell Endocrinol.*, 93:107-16.

Gainsford et al., (1996), "Leptin Can Induce Proliferation, Differentiation, and Functional Activation of Hemopoietic Cells," *Proc. Natl. Acad. Sci. USA*, 93:14564-14568.

Gammon et al., (1992), "Endogenous Loading of HLA-A2 Molecules with an Analog of the Influenza Virus Matrix Protein-Derived Peptide and Its Inhibition By An Exogenous Peptide Antagonist," *J. Immunol.*, 148:7-12.

Ghetie et al., (1990), "Disseminated or Localized Growth of a Human B-Cell Tumor (Daudi) in SCID Mice," *Intl. J. Cancer*, 45:481.

Ghetie et al., (1997), "FcRn: The MHC Class I-Related Receptor that is More Than an IgG Transporter," *Immunology Today*, 18(12):592-598.

Gillies et al., (1991), "Expression of Genetically Engineered Immunoconjugates of Lymphotoxin and a Chimeric Anti-Ganglioside GD2 Antibody," *Hybridomas*, 10(3):347-56.

Goldwasser et al., (1971), "Purification of Erythropoietin," *Proc. Natl. Acad. Sci. USA*, 68:697-8.

Goldwasser et al., (1975), "Erythropoeitin: Assay and Study of its Mode of Action," *Methods Enzymol.*, 37(Ptb):109-21.

Halin et al., (2002), "Enhancement of the Antitumor Activity of Interleukin-12 by Targeted Delivery to Neovasculature," *Nature Biotechnology*, 20:264-269.

Handgretinger et al., (2001), "Immunological Aspects of Haploidentical Stem Cell Transplantation in Children," *Ann. NY Acad. Sci.*, 938:340-57.

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Henikoff et al., (1992), "Amino Acid Substitution Matrices from Protein Blocks," *Proc. Natl. Acad. Sci. USA*, 89:10915-10919.

Hilgers et al., (1999), "Sulfolipo-Cyclodextrin in Squalane-In-Water as a Novel and Safe Vaccine Adjuvant," *Vaccine*, 17:219-28.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Hulett et al., (1994), "Molecular Basis of Fc Receptor Function," *Adv. Immunol.*, 57:1127.

Huston et al., (1988), "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879.

Isaacs et al., (1998), "Therapy with Monoclonal Antibodies. II. The Contribution of Fcγ Receptor Binding and the Influence of CH1 and CH3 Domains on in Vivo Effector Funcion," *J. Immunol.*, 161:3862-3869.

Jacobs et al., (1985), "Isolation and Characterization of Genomic And CDNA Clones of Human Erythropoietin," *Nature*, 313:806-10.

Jefferis et al., (1990), "Molcular Definition of Interaction Sites on Human IgG for Fc Receptors huFcγR," *Mol. Immunol.*, 27(12):1237-1240.

Karlin et al., (1990), "Methods for Assessing the Statistical Significance of Molecular Sequence Features by Using General Scoring Schemes," *Proc. Natl. Acad. Sci. USA*, 87:2264-8.

Karlin et al., (1993), "Applications and Statistics for Multiple High-Scoring Segments in Molecular Sequences," *Proc. Natl. Acad. Sci. USA*, 90:5873-7.

Karpusas et al., (1997), "The Crystal Structure of Human Interferon β at 2.2-A Resolution," *Proc. Natl. Acad. Sci. USA*, 94:11813-11818.

Kelner et al., (1994), "Lymphotactin: A Cytokine that Represents a New Class of Chemokine," *Science*, 266:1395-9.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

Klinman et al., (1997), "Contribution of CPG Motifs to the Immunogenicity of DNA Vaccines," *J. Immunol.*, 158:3635-9.

Kuntz et al., (1982), "A Geometric Approach to Macromolecule-Ligand Interactions," *J. Mol. Biol.*, 161:269-88.

Kurtz, (1982), "A New Candidate for the Regulation of Erythropoiesis. Insulin-Like Growth Factor I," *FEBS Lett.*, 149(1):105-8.

Lai et al., (1986), "Structural Characterization of Human Erythropoietin," *J. Biol. Chem.*, 261:3116-21.

Lai et al., (1998), "DNA Vaccines," *Crit. Rev. Immunol.*, 18:449-84.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lawn et al., (1981), "DNA Sequence of a Major Human Leukocyte Interferon Gene," *Proc. Natl. Acad. Sci. USA*, 78:5435-9.

Lin et al., (1985), "Cloning and Expression of the Human Erythropoietin Gene," *Proc. Natl. Acad. Sci. USA*, 82:7580-4.

Lin et al., (1986), "Monkey Erythropoietin Gene: Cloning, Expression and Comparison with the Human Erythropoietin Gene," *Gene*, 44:201-9.

Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lorenz et al., (1999), "Induction of Anti-Tumor Immunity Elicited by Tumor Cells Expressing a Murine LFA-3 Analog Via a Recombinant Vaccinia Virus," *Hum. Gene Ther.*, 10:623-31.

Lotze et al., (1996), "Cytokine Gene Therapy of Cancer Using Interleukin-12: Murine and Clinical Trials," *Ann. NY Acad. Sci.*, 795:440-54.

Macdougall et al., (1999), "Pharmacokinetics of Novel Erythropoiesis Stimulating Protein Compared with Epoetin Alfa in Dialysis Patients," *J. Am. Soc. Nephrol.*, 10:2392-5.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.*, 11:765-74.

Maloy et al., (2001), "Regulatory T Cells in the Control of Immune Pathology," *Nature Immunol.*, 2:816-22.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Marshall et al., (1995), "Prediction of Peptide Affinity to HLA-DR Molecules," *Biomed. Pept. Proteins Nucleic Acids*, 1(3):157-62.

Marshall, K.W., (1994), "Role of the Polymorphic Residues in HLA-DR Molecules in Allele-Specific Binding of Peptide Ligands," *J. Immunol.*, 152:4946-57.

Martin et al., (2001), "Crystal Structure at 2.8 Å of an FcRn/Heterodimeric Fc Complex: Mechanism of pH-Dependent Binding," *Mol. Cell.*, 7(4):867-77.

McDonald, (1986), "Cloning, Sequencing, and Evolutionary Analysis of the Mouse Erythropoietin Gene," *Mol. Cell. Biol.*, 6:842-8.

McGonigle et al., (1984), "Erythropoietin Deficiency and Inhibition of Erythropoiesis in Renal Insufficiency," *Kidney Int.*, 25(2):437-44.

McMahan et al., (1991), "A Novel IL-1 Receptor, Cloned From B-Cells by Mammalian Expression is Expressed in Many Cell Types," *EMBO J.*, 10:2821-32.

McMahon et al., (1990), "Pharmacokinetics and Effects of Recombinant Human Erythropoietin after Intravenous and Subcutaneous Injections in Healthy Volunteers," *Blood*, 76:1718-22.

Mehrotra et al., (1993), "Effects of IL-12 on the Generation of Cytotoxic Activity in Human CD8+ T Lymphocytes," *J. Immunol.*, 151:2444-52.

Menard et al., (1983), "Generation of Monoclonal Antibodies Reacting with Normal and Cancer Cells of Human Breast," *Cancer Res.*, 43:1295-300.

Miyake et al., (1977), "Purification of Human Erythropoietin," *J. Biol. Chem.*, 252:5558-64.

Morrison et al., (1984), "Chimeric Human Antibody Molecules: Mouse Antigen-Binding Domains with Human Constant Region Domains," *Proc. Natl. Acad. Sci. USA*, 81:6851-5.

Nagao et al., (1992), "Nucleotide Sequence of Rat Erythropoietin," *Biochim. Biophys. Acta*, 1171(1):99-102.

Nastala et al., (1994), "Recombinant IL-12 Administration Induces Tumor Regression in Association with IFN-Gamma Production," *J. Immunol.*, 153:1697-706.

Naughton et al., (1983), "Evidence for an Erythropoietin-Stimulating Factor in Patients with Renal and Hepatic Disease," *Acta. Haematol.*, 69:171-9.

Noguchi et al., (1994), "A Mouse Mutant P53 Product Recognized by CD4+ and CD8+ T Cells," *Proc. Natl. Acad. Sci. USA*, 91:3171-5.

Orlandi et al., (1989), "Cloning Immunoglobulin Variable Domains for Expression by the Polymerase Chain Reaction," *Proc. Natl. Acad. Sci. USA*, 86:3833-7.

Palmer et al., (2001), "Phase I Study of the BLP 25 (MUC1 Peptide) Liposomal Vaccine for Active Specific Immunotherapy in Stage IIIB/IV Non-Small-Cell Lung Cancer," *Clinical Lung Cancer*, 3(1):49-57.

Palucka et al., (1998), "Dendritic Cells as the Terminal Stage of Monocyte Differentiation," *J. Immunol.*, 160:4587-95.

Panina-Bordignon et al., (1989), "Universally Immunogenic T Cell Epitopes: Promiscuous Binding to Human MHC Class II and Promiscuous *Recognition* by T Cells," *Eur. J. Immunol.*, 19:2237-42.

Pavlovic-Kentera et al., (1980), "Effects of Prostaglandin Synthetase Inhibitors, Salt Overload and Renomedullary Dissection on the Hypoxia Stimulated Erythropoietin Production in Rats," *Expt. Hematol.*, 8(Supp. 8):283-92.

Pedley et al. (1999), "Enhancement of Antibody-Directed Enzyme Prodrug Therapy in Colorectal Xenografts by an Antivascular Agent," *Cancer Res.*, 59:3998-4003.

Perussia et al., (1992), "Natural Killer (NK) Cell Stimulatory Factor or IL-12 Has Differential Effects on the Proliferation of TCR-Alpha Beta+, TCR-Gamma Delta+ T Lymphocytes, and NK Cells," *J. Immunol.*, 149:3495-502.

Pluschke et al., (1996), "Molecular Cloning of a Human Melanoma-Associated Chondroitin Sulfate Proteoglycan," *Proc. Natl. Acad. Sci. USA*, 93:9710-5.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Radhakrishnan et al., (1996), "Zinc Mediated Dimer of Human Interferon-Alpha 2b Revealed by X-Ray Crystallography," *Structure* 4:1453-63.

Ramachandran et al., (1968)"Conformation of Polypeptides and Proteins," *Adv. Prot. Chem.*, 23:283-438. (1968) (At pp. 285-294).

Rarey et al., (1995), "Time-Efficient Docking of Flexible Ligands into Active Sites Of Proteins," *Proc. Int. Conf. Intell. Syst. Mol. Biol.* 3:300-8.

Resegotti et al., (1981), "Treatment of Aplastic Anaemia with Methenolone, Stanozolol and Nandrolone. A Report of 130 Cases," *Panminerva Med.*, 23:243-8.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Rothmann et al., (1982), "Erythropoietin-Dependent Erythrocytosis associated with Hepatic Angiosarcoma," *J. Surg. Oncol.*, 20:105-8.

Runkel et al., (1998), "Structural and Functional Differences Between Glycosylated and Non-Glycosylated Forms of Human Interferon-β(IFN-β)," *Pharmaceutical Res.*, 15:641-649.

Sakano et al., (1980), "Two Types of Somatic Recombination are Necessary for the Generation of Complete Immunoglobin Heavy-Chain Genes," *Nature*, 286:676-683.

Sali et al., (1993), "Comparative Protein Modelling by Satisfaction of Spatial Restraints," *J. Mol. Biol.*, 234:779-815.

Schecter et al., (1997), "Tissue Factor is Induced by Monocyte Chemoattractant Protein-1 in Human Aortic Smooth Muscle and THP-1 Cells," *J. Biol. Chem.*, 272:28568-73.

Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.

Sharp et al., (1988), "Codon Usage Patterns in *Escherichia coli, Bacillus subtilis, Saccharomyces cerevisiae, Schizosaccharomyces pombe, Drosophila melanogaster and Homo sapiens*; a Review of the Consdierable Within-Species Diversity," *Nucleic Acids Res.*, 16(17):8207-8211.

Simonsen et al., (1983), "Isolation and Expression of an Altered Mouse Dihydrofolate Reductase cDNA," *Proc. Natl. Acad. Sci. USA*, 80:2495-2499.

Smith et al., (1981), "Identification of Common Molecular Subsequences," *J. Mol. Biol.*, 147:195-197.

Soligo et al., (1998), "Expansion of Dendritic Cells Derived from Human CD34+ Cells in Static And Continuous Perfusion Cultures," *Br. J. Haematol.*, 101:352-63.

Spivak et al., (1989), "The In Vivo Metabolism of Recombinant Human Erythropoietin in The Rat," *Blood*, 73:90-9.

Sturniolo et al., (1999), "Generation of Tissue-Specific and Promiscuous HLA Ligand Databases Using DNA Microarrays and Virtual HLA Class II Matrices," *Nat. Biotech.*, 17(6):555-61.

Suliman et al., (1996), "Cloning of a CDNA Encoding Bovine Erythropoietin and Analysis of Its Transcription in Selected Tissues," *Gene*, 171:275-80.

Takahashi et al. (2000), "Immunologic Self-Tolerance Maintained by CD25=0 CD4=0 Regulatory T Cells Constitutively Expressing Cytotoxic T Lymphocyte-Associated Antigen," *J. Exp. Med.*, 192(2):303-309.

Takai, (2002), "Roles of Fc Receptors in Autoimmunity," *Nat. Rev. Immunol.*, 2(8):580-92.

Taniguchi et al., (1980), "Expression of the Human Fibroblast Interferon Gene in *Escherichia coli* " *Proc. Natl. Acad. Sci. USA*, 77:5230-5233.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Nat. Acad. Sci. USA*, 93:250-4.

Van Den Eynde et al., (1989), "Presence on a Human Melanoma of Multiple Antigens Recognized by Autologous CTL," *Int. J. Cancer*, 44:634-40.

Van Der Bruggen et al., (1991), "A Gene Encoding an Antigen Recognized by Cytolytic T Lymphocytes on a Human Melanoma," *Science*, 254:1643-7.

Van Heyningen et al., (1982), "Human MHC Class II Molecules as Differentiation Markers," *Immunogenetics*, 16:459-69.

Voest et al., (1995), "Inhibition of Angiogenesis in Vivo by Interleukin 12," *J. Natl. Canc. Inst.*, 87:581-6.

Von Heijne et al., (1986), "A New Method for Predicting Signal Sequence Cleavage Sites," *Nucleic Acid Res.*, 14:4683-4690.

Ward et al., (1995), "The Effector Functions of Immunoglobulins: Implications for Therapy," *Therapeutic. Immunology*, 2:77-94.

Watson et al., (1984), "Compilation of Published Signal Sequences," *Nucleic Acid Res.*, 12:5145-5164.

Weitkamp et al., (1973), "Additional Data on the Population Distribution of Human Serum Albumin Genes; Three New Variants," *Ann. Hum. Genet.*, 37:219-26.

Wetzel et al., (2001), "BAY50-4798, an Interleukin-2 (IL_2) Variant, demonstrates Selective Activation of Human and Chimpanzee T Cells Relative to NK Cells but Shows Less Selectivity for T Cells from Monkeys and Rodents," *ASCO Annual Meeting*, Abstract 1051.

Woof et al., (1986), "Localisation of the Monocyte-Binding Region on Human Immunoglobulin G," *Mol. Immunol.*, 23:319-30.

Wu et al., (1997), "Suppression of Tumor Growth with Recombinant Murine Angiostatin," *Biochemical and Biophysical Research Communications*, 236:651-654.

Wyatt et al., (1998), "The Antigenic Structure of the HIV Gp120 Envelope Glycoprotein," *Nature*, 393:705-11.

Wysocka et al., (1995), "Interleukin-12 is Required for Interferon-Gamma Production and Lethality in Lipopolysaccharide-Induced Shock in Mice," *Eur. J. Immunol.*, 25:672-6.

Yan et al., (1996), "Characterization of an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhang et al., (1994), "Structure/Activity Analysis of Human Monocyte Chemoattractant Protein-1 (MCP-1) by Mutagenesis. Identification of a Mutated Protein that Inhibits MCP-1-Mediated Monocyte Chemotaxis," *J. Biol. Chem.*, 269:15918-24.

Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.

Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.

Batova et al., "The Ch14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263 (1999).

International Search Report for WO01/58957, completed Jan. 3, 2002, 4 pgs.

Figure 4 (J774 binding)

ENHANCING THE CIRCULATING HALF-LIFE OF ANTIBODY-BASED FUSION PROTEINS

RELATED APPLICATIONS

This application is a divisional application of prior U.S. application Ser. No. 11/268,191, filed Nov. 7, 2005, issued as U.S. Pat. No. 7,507,406 on Mar. 24, 2009, which is a divisional application of U.S. application Ser. No. 09/780,668, filed Feb. 9, 2001, issued as U.S. Pat. No. 7,091,321 on Aug. 15, 2006, which claims priority to, and the benefit of U.S. provisional patent application 60/181,768, filed Feb. 11, 2000, the disclosures of each of which are incorporated by reference herein.

FIELD OF THE INVENTION

The present invention relates generally to fusion proteins. More specifically, the present invention relates to methods of enhancing the circulating half-life of antibody-based fusion proteins.

BACKGROUND OF THE INVENTION

The use of antibodies for treating human diseases is well established and has become more sophisticated with the introduction of genetic engineering. Several techniques have been developed to improve the utility of antibodies. These include: (1) the generation of monoclonal antibodies by cell fusion to create "hybridomas", or by molecular cloning of antibody heavy (H) and light (L) chains from antibody-producing cells; (2) the conjugation of other molecules to antibodies to deliver them to preferred sites in vivo, e.g., radioisotopes, toxic drugs, protein toxins, and cytokines; (3) the manipulation of antibody effector functions to enhance or diminish biological activity; (4) the joining of other proteins such as toxins and cytokines with antibodies at the genetic level to produce antibody-based fusion proteins; and (5) the joining of one or more sets of antibody combining regions at the genetic level to produce bi-specific antibodies.

Proteins can be joined together through either chemical or genetic manipulation using methods known in the art. See, for example, Gillies et al., *Proc. Natl. Acad. Sci.* USA 89:1428-1432 (1992); and U.S. Pat. No. 5,650,150.

However, the utility of recombinantly-produced antibody-based fusion proteins may be limited by their rapid in vivo clearance from the circulation. Antibody-cytokine fusion proteins, for example, have been shown to have a significantly lower in vivo circulating half-life than the free antibody. When testing a variety of antibody-cytokine fusion proteins, Gillies et al. reported that all of the fusion proteins tested had an α phase (distribution phase) half-life of less than 1.5 hours. Indeed, most of the antibody-based fusion proteins were cleared to 10% of the serum concentration of the free antibody by two hours. See, Gillies et al., BIOCONJ. CHEM. 4: 230-235 (1993). More recently, it was shown that antibody-based fusion proteins with reduced binding affinity for an Fc receptor have enhanced circulating half-lives. It was also shown that a reduced binding affinity for the Fc receptor interfered with some of the antibody effector functions such as antibody-dependent cellular cytotoxicity (ADCC), but did not interfere with other functions such as complement fixation or antigen binding. See Gillies at al., Cancer Res. 59(9):2159-66 (1999).

In some cases, such as the treatment of cancer or viral diseases, it would be desirable to maintain antibody effector functions and long circulating half-life. Therefore, there is a need in the art for additional methods of enhancing the in vivo circulating half-life of antibody-based fusion proteins.

SUMMARY OF THE INVENTION

Immunoglobulin G (IgG) molecules interact with multiple classes of cellular receptors including three classes of Fcγ receptors (FcγR) specific for the IgG class of antibody, namely FcγRI, FcγRII and FcγRIII. They also interact with the FcRp class of receptor in a pH-dependent manner with little or no binding at neutral pH but high binding at a pH of 6.0.

The serum half-life of an antibody is influenced by the ability of that antibody to bind to an Fc receptor (FcR) and to the Fc protection receptor (FcRp). The serum half-life of immunoglobulin fusion proteins is also influenced, for example, by the ability to bind to such receptors (Gillies et al., Cancer Res. 59:2159-66 (1999)).

The invention discloses the surprising observation that, within fusion proteins comprising an immunoglobulin (Ig) moiety and a non-immunoglobulin (non-Ig) moiety, alteration of amino acids near the junction of the two moieties dramatically increases the serum half-life of the fusion protein. The observation is surprising because the amino acid changes affect protein surfaces that are distinct from the interaction surfaces of the Fc region with the Fc receptors and with the Fc protection receptor. In addition, the amino acid changes of the invention have their effect even when the known Fc receptor and Fc protection receptor are not primarily determining the serum half-life of the fusion protein. Thus, the amino acid alterations of the invention can be combined with amino acid alterations affecting the interaction with Fc receptor and/or Fc protection receptor to achieve synergistic effects.

The present invention provides fusion proteins containing an immunoglobulin in which the serum half-life is improved as a result of alterations that are at sites distinct from the Fc region's interaction surface with Fc receptor and Fc protection receptor (FcRp). The present invention also provides methods for the production of fusion proteins between an immunoglobulin moiety and a second, non-immunoglobulin protein having an improved serum half-life.

The alterations in the amino acid sequence of the fusion protein are preferentially at the junction of the Ig moiety and the non-Ig moiety. The junction region of the fusion protein contains alterations that, relative to the naturally occurring sequences of the Ig heavy chain and non-Ig protein, preferably lie within about 10 amino acids of the junction point. More preferably, the amino acid changes cause an increase in hydrophobicity. Even more preferably, the amino acid changes involve changing the C-terminal lysine of the antibody moiety to a hydrophobic amino acid such as alanine or leucine. In a preferred embodiment, the fusion protein of the invention comprises an Ig heavy chain, preferably located N-terminal to a second, non-Ig protein.

In another embodiment of the invention, the binding affinity of fusion proteins for FcRp is optimized by alteration of the interaction surface of the Fc moiety that contacts FcRp. The important sequences for the binding of IgG to the FcRp receptor have been reported to be located in the CH2 and CH3 domains. According to the invention, alterations of the fusion junction in a fusion protein are combined with alterations of Fc's interaction surface with FcRp to produce a synergistic effect. In some cases it may be useful to increase the interaction of the Fc moiety with FcRp at pH 6, and it may also be useful to decrease the interaction of the Fc moiety with FcRp at pH 8. Such modifications include alterations of residues necessary for contacting Fc receptors or altering others that affect the contacts between other heavy chain residues and the FcRp receptor through induced conformational changes. Thus, in a preferred embodiment, an antibody-based fusion protein with enhanced in vivo circulating half-life is obtained by first linking the coding sequences of an Ig constant region and a second, non-immunoglobulin protein and then introducing a mutation (such as a point mutation, a deletion, an insertion, or a genetic rearrangement) in an IgG constant region at or near one or more amino acid selected from Ile 253, His 310 and His 435. The resulting antibody-based fusion proteins have a longer in vivo circulating half-life than the unmodified fusion proteins.

In certain circumstances it is useful to mutate certain effector functions of the Fc moiety. For example, complement fixation may be eliminated. Alternatively or in addition, in another set of embodiments the Ig component of the fusion protein has at least a portion of the constant region of an IgG that has reduced binding affinity for at least one of FcγRI, FcγRII or FcγRIII. For example, the gamma4 chain of IgG may be used instead of gamma 1. The alteration has the advantage that the gamma4 chain results in a longer serum half-life, functioning synergistically with one or more mutations at the fusion junction. Accordingly, IgG2 may also be used instead of IgG1. In an alternative embodiment of the invention, a fusion protein includes a mutant IgG1 constant region, for example an IgG1 constant region having one or more mutations or deletions of $Leu_{234}$, $Leu_{235}$, $Gly_{236}$, $Gly_{237}$, $Asn_{297}$, or $Pro_{331}$. In a further embodiment of the invention, a fusion protein includes a mutant IgG3 constant region, for example an IgG3 constant region having one or more mutations or deletions of $Leu_{281}$, $Leu_{282}$, $Gly_{283}$, $Gly_{284}$, $Asn_{344}$, or $Pro_{378}$. However, for some applications, it may be useful to retain the effector function that accompanies Fc receptor binding, such as ADCC.

In a preferred embodiment, the second, non-immunoglobulin moiety of the fusion protein is a cytokine. The term "cytokine" is used herein to describe naturally occurring or recombinant proteins, analogs thereof, and fragments thereof which elicit a specific biological response in a cell which has a receptor for that cytokine. Preferably, cytokines are proteins that may be produced and excreted by a cell. Cytokines preferably include interleukins such as interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), granulocyte colony stimulating factor (G-CSF) and erythropoietin, tumor necrosis factors (TNF) such as TNFα, lymphokines such as lymphotoxin, regulators of metabolic processes such as leptin, interferons such as interferon α, interferon β, and interferon γ, and chemokines. Preferably, the antibody-cytokine fusion protein of the present invention displays cytokine biological activity.

In an alternative preferred embodiment, the second, non-immunoglobulin moiety of the fusion protein is a ligand-binding protein with biological activity. Such ligand-binding proteins may, for example, (1) block receptor-ligand interactions at the cell surface; or (2) neutralize the biological activity of a molecule (e.g., a cytokine) in the fluid phase of the blood, thereby preventing it from reaching its cellular target. Preferably, ligand-binding proteins include CD4, CTLA-4, TNF receptors, or interleukin receptors such as the IL-1 and IL-4 receptors. Preferably, the antibody-receptor fusion protein of the present invention displays the biological activity of the ligand-binding protein.

In yet another alternative preferred embodiment, the second, non-immunoglobulin moiety of the fusion protein is a protein toxin. Preferably, the antibody-toxin fusion protein of the present invention displays the toxic activity of the protein toxin.

In yet other preferred embodiments, the second, non-immunoglobulin moiety of the fusion protein is a hormone, neurotrophin, body-weight regulator, serum protein, clotting factor, protease; extracellular matrix component, angiogenic factor, anti-angiogenic factor, or another secreted protein or secreted domain. For example, CD26, IgE receptor, polymeric IgA receptor, other antibody receptors, Factor VIII, Factor IX, Factor X, TrkA, PSA, PSMA, Flt-3 Ligand, endostatin, angiostatin, and domains of these proteins.

In yet other embodiments, the second, non-immunoglobulin moiety is a non-human or non-mammalian protein. For example, HIV gp120, HIV Tat, surface proteins of other viruses such as adenovirus, and RSV, other HIV components, parasitic surface proteins such as malarial antigens, and bacterial surface proteins are preferred. These non-human proteins may be used, for example, as antigens, or because they have useful activities. For example, the second, non-immunoglobulin moiety may be streptokinase, staphylokinase, urokinase, tissue plasminogen activator, or other proteins with useful enzymatic activities.

According to the invention, the non-immunoglobulin moiety can be a portion of a protein. Preferably, the non-Ig protein moiety is a protein portion that substantially retains the functional and or structural properties of an intact protein. In a preferred embodiment, the non-Ig protein moiety is a functional or structural portion of a protein described herein.

In a preferred embodiment, the antibody-based fusion protein comprises a variable region specific for a target antigen as well as a constant region, either of which is linked through a peptide bond to a second, non-immunoglobulin protein. The constant region may be the constant region normally associated with the variable region, or a different one, e.g., variable and constant regions from different species. The heavy chain may include any combination of one or more CH1, CH2, or CH3 domains. Preferably, the heavy chain includes CH1, CH2, and CH3 domains, and more preferably, only CH2 and CH3 domains. In one embodiment, the antibody-based one fusion protein comprises an Fv region with fused heavy and light chain variable regions. Also embraced within the term "fusion protein" are constructs having a binding domain comprising framework regions and variable regions (i.e., complementarity determining regions) from different species, such as are disclosed by Winter, et al., Great Britain Patent No. 2,188,638. Antibody-based fusion proteins comprising a variable region preferably display antigen-binding specificity. In yet another preferred embodiment, the antibody-based fusion protein further comprises a light chain. The invention thus provides fusion proteins in which the antigen-binding specificity and activity of an antibody are combined with the potent biological activity of a second, non-immunoglobulin protein, such as a cytokine. A fusion protein of the present invention can be used to deliver selectively the second, non-immunoglobulin protein to a target cell in vivo so that the second, non-immunoglobulin protein can exert a localized biological effect.

In an alternative preferred embodiment, the antibody-based fusion protein comprises a heavy chain constant region linked through a peptide bond to a second, non-immunoglobulin protein, but does not comprise a heavy chain variable region. The invention thus further provides fusion proteins which retain the potent biological activity of a second, non-immunoglobulin protein, but which lack the antigen-binding specificity and activity of an antibody.

In preferred embodiments, the fusion protein comprises two chimeric chains comprising at least a portion of a heavy chain and a second, non-Ig protein linked by a disulfide bond.

In preferred embodiments, the fusion proteins of the invention are useful to treat cancer, viral infections, immune disorders, and to enhance the growth (including proliferation) of specific cell types.

The invention also features DNA constructs encoding the above-described fusion proteins, and cell lines, e.g., myelomas, transfected with these constructs.

These and other objects, along with advantages and features of the invention disclosed herein, will be made more apparent from the description, drawings, and claims that follow.

DETAILED DESCRIPTION OF THE INVENTION

Figure 1A:
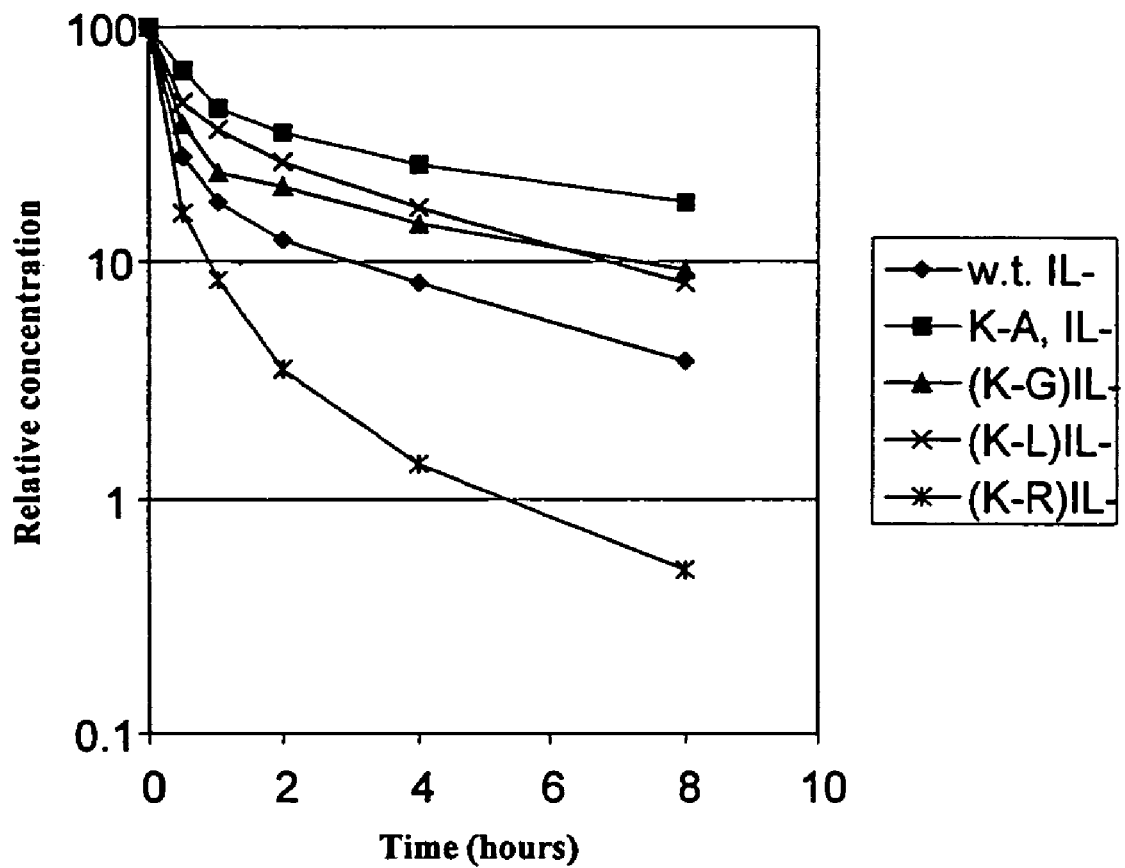
FIG. 1 shows the pharmacokinetic behavior of the KS-IL-2 fusion protein and various mutant fusion proteins containing substitutions of the antibody heavy chain's C-terminal lysine moiety or other alterations described in the Examples. Levels of antibody or fusion protein were measured by an ELISA that tests for IL-2 (FIG. 1A) or human Fc (FIG. 1B).

The present invention provides antibody fusion proteins having one or more mutations at the junction between the Ig and non-Ig moieties which increase the circulating half lives of the fusion proteins. The mutant fusion proteins of the invention have the advantageous property that their serum half-life is improved without affecting the interaction of the antibody moiety with either of the two known pharmacokinetic-determining receptors in the body: Fc receptor and FcRp.

In general, an antibody-based fusion protein of the invention comprises a portion of an immunoglobulin (Ig) protein joined to a non-immunoglobulin (non-Ig) protein, such that the amino acid sequence of the region spanning the junction between the Ig and non-Ig proteins has at least one mutation when compared to the wild-type amino acid sequences of the Ig and non-Ig proteins.

In one embodiment, at least one mutation is in the C-terminal region of the Ig portion. In another embodiment, at least one mutation is in the N-terminal region of the non-Ig protein. In a further embodiment, the fusion protein contains at least one mutation in the C-terminal region of the Ig portion, and at least one mutation in the N-terminal region of the non-Ig protein. A mutation may be a point mutation, an insertion, a deletion, or a gene rearrangement. In preferred embodiments the mutation increases the hydrophobicity of the junction region. For example, the mutation replaces a charged or ionizable amino acid with a non-charged or hydrophobic amino acid (e.g., a Lys, Arg or other ionizable residue is replaced with an Ala, Leu, Gly, Trp or other non-charged or hydrophobic residue).

In an optional embodiment, a spacer or linker peptide is inserted between the Ig and non-Ig proteins. The spacer or linker peptide is preferably non-charged, more preferably non-polar, and or hydrophobic. The length of a spacer or linker peptide is preferably between 1 and about 100 amino acids, more preferably between 1 and about 50 amino acids, or between 1 and about 25 amino acids, and even more preferably between 1 and about 15 amino acids. In another embodiment of the invention, the Ig and non-Ig moieties of the fusion protein are joined via a spacer or linker peptide, and there is at least one mutation in either one or both of the Ig and non-Ig moieties. In an alternative embodiment of the invention, the Ig and non-Ig moieties are separated by a synthetic spacer, for example a PNA spacer, that is preferably non-charged, more preferably non-polar, and or hydrophobic.

According to the invention, an immunoglobulin (Ig) chain is an immunoglobulin protein or a portion of an immunoglobulin protein that includes a variable or a constant domain. An Ig chain is preferably a portion of an immunoglobulin heavy chain, for example, an immunoglobulin variable region capable of binding a preselected cell-type. In a preferred embodiment, the Ig chain comprises a variable region specific for a target antigen as well as a constant region. The constant region may be the constant region normally associated with the variable region, or a different one, e.g., variable and constant regions from different species. In a more preferred embodiment, an Ig chain includes a heavy chain. The heavy chain may include any combination of one or more CH1, CH2, or CH3 domains. Preferably, the heavy chain includes CH1, CH2, and CH3 domains, and more preferably only CH2 and CH3 domains. In one embodiment, the portion of the immunoglobulin includes an Fv region with fused heavy and light chain variable regions.

According to the invention, a non-immunoglobulin protein includes a naturally occurring protein that is not an immunoglobulin, or a synthetic or recombinant protein that is not an immunoglobulin, or a fragment of any of the above. In a preferred embodiment, a non-immunoglobulin protein includes a functional domain such as a ligand binding domain, an enzymatic domain, a regulatory domain, or a domain that interacts with one or more cellular factors. In an alternative embodiment, a non-immunoglobulin domain comprises a structural domain or an epitope.

In a preferred embodiment, the Ig chain is joined to the non-Ig protein via a gene fusion. Preferably, the gene fusion is synthetic or recombinant, and is generated using standard techniques of chemical synthesis or molecular biology. Typically, a mutation is introduced as part of the gene fusion construct. Alternatively, a mutation may be introduced subsequently, using known methods of mutagenesis (for example by exposing the gene fusion construct to irradiation, or chemical or biological mutagenesis).

According to the invention, a junction region is the region of the fusion protein surrounding the junction point between the Ig and non-Ig moieties of the fusion protein. In a preferred embodiment, the junction region includes the C-terminal portion of the Ig moiety and the N-terminal portion of the non-Ig moiety. In one embodiment, the junction region also comprises a spacer or linker peptide inserted at the junction point between the Ig and non-Ig moieties.

According to preferred embodiments of the invention, a mutation in the Ig moiety is in the C-terminal portion of the Ig moiety, preferably within about 100 residues, more preferably within about 50 residues, or about 25 residues, and even more preferably within about 10 residues from the C-terminus of the Ig moiety.

According to preferred embodiments of the invention, a mutation in the non-Ig moiety is in the N-terminal portion of the non-Ig moiety, preferably within about 100 residues, more preferably within about 50 residues, or about 25 residues, and even more preferably within about 10 residues from the N-terminus of the non-Ig moiety.

In preferred embodiments of the invention, a mutation is in the C-terminal region of the Ig moiety, but the mutation is not in part of the Ig protein that interacts with the Fc receptor (FcR) or FcRp.

An antibody fusion protein having a mutation according to the invention has an increased in vivo circulating half-life when compared to the circulating half-life of a corresponding antibody fusion protein without the mutation. The circulating half-life of an antibody fusion protein can be measured by assaying the serum level of the fusion protein as a function of time.

Experimental evidence indicates that the effects of preferred mutations of the invention are not dependent on interactions with FcR or FcRp. First, preferred mutations that increase the circulating half-life of a fusion protein do not affect regions of the antibody that, on the three dimensional structure, are part of the interaction surface that binds to FcR or to FcRp. Second, preferred mutations of the invention can cause an improvement in serum half-life even when the interaction with FcR is removed by use of an IgG-gamma4 chain and the interaction with FcRp is removed by performing the pharmacokinetic study in a beta2-microglobulin mutant mouse in which FcRp is defective. Third, preferred mutations of the invention do not significantly affect the binding of Ig fusion proteins to FcR on J774 cells.

Site-directed mutagenesis analyses indicate that the surface of Fc that interacts with the Fc receptor is near the hinge region on the CH2 domain. The Fc region's FcR interaction surface is very far, in three dimensions, from the C-terminus of Fc. Similar analyses indicate that FcRp interacts with amino acid residues located at the interface between the CH2 and CH3 domains.

FcRp binds its ligand with a much higher affinity at acidic pH (pH 6.0), than at neutral or slightly basic pH (pH 7.4). This is consistent with the role of FcRp in protecting Fc containing molecules such as antibodies following their cellular internalization within endosomes. These cellular compartments become acidified after fusion with lysosomes and their protein constituents are degraded by acidic proteases. Binding to membrane bound FcRp during this process prevents degradation of the antibody and allows it to be recycled to the outside of the cell (back into the circulation) or across a cell layer (a process called transcytosis). This latter process allows IgG to pass through the neonatal intestinal mucosa following the ingestion of milk in the acidic environment of the gut.

The structure of the Fc/FcRp complex indicates that FcRp binds to the side of the Fc region, with contacts in both the CH2 and CH3 domains, and that the contacted region is not particularly close to the C-terminus of the Fc region. Thus, alteration of the very C-terminal region of the Fc is not expected to alter the interaction with FcRp.

Not wishing to be bound by any particular theory, it is believed that mutations in the fusion junction region that increase the circulatory half life of a fusion protein according to the invention also reduce cleavage of the fusion protein in a protease cleavage assay, as illustrated in Example 15. It is further believed that protease digestion may contribute to the disappearance of intact proteins form the body, including fusion proteins. Thus, resistance to proteases may directly contribute to improved pharmacokinetics of proteins. It is also further believed that protease digestion of non-denatured proteins involves access by a protease to an exposed sequence in the correct conformation, as well as recognition of a specific sequence of amino acids. Thus, mutations in the fusion junction that affect the general conformation of a protein and thus affect accessibility of proteases to their cleavage sites may contribute to protease resistance and to improved pharmacokinetics. In addition, mutations that alter specific protease recognition sequences may contribute to protease resistance and to improved pharmacokinetics.

A feature of mutations of the invention is that they can be combined with other mutations or substitutions in the antibody moiety to synergistically modulate serum half-life or other properties of the Ig moiety. For example, one or more mutations of the invention that increase the circulating half-life of an antibody fusion protein can be combined with one or more mutations that affect the interaction between the antibody fusion protein and FcR or FcRp.

In addition, the mutations of the invention can be used with a wide variety of antibody moieties and with a wide variety of non-Ig fusion partners. The immunoglobulins include IgG, IgM, IgA, IgD, and IgE. The non-Ig fusion partners include cytokines, other secreted proteins, enzymes, or soluble fragments of transmembrane receptors, such as ligand-binding domains.

According to the invention, an antibody-based fusion protein with an enhanced in vivo circulating half-life can be further enhanced by modifying within the Fc portion itself. These may be residues including or adjacent to Ile 253, His 310 or His 435 or other residues that can effect the ionic environments of these residues when the protein is folded in its 3-dimensional structure. The resulting proteins can be tested for optimal binding at pH 6 and at pH 7.4-8 and those with high levels of binding at pH 6 and low binding at pH 8 are selected for use in vivo. Such mutations can be usefully combined with the junction mutations of the invention.

Methods and compositions of the invention are useful when coadministered with angiogenesis inhibitors such as those disclosed in PCT/US99/08335 (WO 99/52562) or prostaglandin inhibitors such as those disclosed in PCT/US99/08376 (WO 99/53958). Methods and compositions of the invention can also be used in multiple cytokine protein complexes such as those disclosed in PCT/US00/21715. Methods and compositions of the invention are also useful in combination with other mutations disclosed in PCT/US99/03966 (WO 99/43713) that increase the circulating half-life of a fusion protein.

Non-limiting methods for synthesizing useful embodiments of the invention are described in the Examples herein, as well as assays useful for testing pharmacokinetic activities, both in vitro and in pre-clinical in vivo animal models. The preferred gene construct encoding a chimeric chain includes, in 5' to 3' orientation, a DNA segment which encodes at least a portion of an immunoglobulin and DNA which encodes a second, non-immunoglobulin protein. An alternative preferred gene construct includes, in 5' to 3' orientation, a DNA segment which encodes a second, non-immunoglobulin protein and DNA which encodes at least a portion of an immunoglobulin. The fused gene is assembled in or inserted into an expression vector for transfection of the appropriate recipient cells where it is expressed.

The invention also provides methods for identifying mutations that increase the circulatory half-life of an antibody-based fusion protein. The methods comprise introducing one or more mutations in a region spanning the junction between the Ig moiety and the non-Ig moiety of an antibody-based fusion protein. The circulating half-life of the mutated fusion protein is assayed, preferably by monitoring its serum level in vivo as a function of time.

In one embodiment of the invention, a mutation that increases the circulatory half-life of an antibody-based fusion protein is a mutation that reduces cleavage of the fusion protein in a protease cleavage assay, as discussed in Example 15. The mutation is preferably a mutation in a region spanning the junction between the Ig moiety and the non-Ig moiety of the fusion protein (for example, a mutation in the junction region discussed above). Alternatively, the mutation may be any mutation in the fusion protein that reduces protease cleavage and increases the circulatory half life of the fusion protein, as described in Example 16. Accordingly, the invention provides methods for screening mutations in proteins in general, and preferably in an Ig-cytokine fusion protein, to identify mutations that increase the circulatory half-life of the fusion protein.

The invention is illustrated further by the following non-limiting examples. The amino acid residue numbers used herein refer to the IgG1 amino acid sequence. One of ordinary skill in the art will understand that corresponding mutations in fusion proteins involving other Ig proteins are useful to increase their circulating half-lives.

Accordingly, the teachings presented herein are applicable to other Ig molecules such as IgG2, IgG3, IgG4, IgA, IgM, IgD, or IgE.

EXAMPLES

Example 1

Construction of Antibody-IL-2 Genes with Substitutions of the Lys Codon at the Fusion Junction The amino acid sequence at the junction of the antibody-IL-2 fusion protein is SerProGlyLys-AlaProThr (SEQ ID NO: 1), in which the SerProGlyLys (SEQ ID No. 2) is the normal carboxy terminus of the heavy chain of the antibody, and AlaProThr is the N-terminal sequence of mature IL-2. In order to determine the effect alterations in the region of the fusion junction on the pharmacokinetics of the fusion protein, substitutions or deletion of the residue were made by mutagenesis, as described below.

The expression vector for immunocytokines was described in Gillies at al., (1998) J. Immunol. 160:6195-6203. In the human gamma-1 gene encoding the heavy chain, the XmaI restriction site located 280 bp upstream of the translation stop codon was destroyed by introducing a silent mutation (TCC to TCA). Another silent mutation (TCT to TCC) was introduced to the Ser codon three residues upstream of the C-terminal lysine of the heavy chain to create the sequence TCC CCG GGT AAA (SEQ ID No. 3), which contains a new XmaI site [Lo at al, (1998) Protein Engineering 11:495-500]. The IL-2 cDNA was constructed by chemical synthesis and it contains a new and unique PvuII restriction site [Gillies at al., (1992) Proc. Natl. Acad. Sci. 89:1428-1432]. Both the XmaI and PvuII sites are unique in the expression vector, and they facilitated mutagenesis of the lysine codon which lies at the junction of the CH3 and the IL-2 DNA.

Substitution or deletion of the Lys codon was achieved by replacing the XmaI-PvuII fragment in the immunocytokine expression vector with an oligonucleotide duplex encoding the desired mutation. In this case the variable regions of the heavy and light chains were derived from the humanized KS antibody, which recognized a human antigen called EpCAM (Epithelial cell adhesion molecule). The sequences of the oligonucleotide duplexes used in the present invention are listed below, where the codons in bold encode the desired mutations, and the sequences in italics, CCCGG and CAG are the cohesive end of the XmaI site and the blunt end of the PvuII site, respectively. The oligonucleotide duplex with 5'-hydroxyl ends were used in the ligation to the XmaI-PvuII digested expression vector. The use of oligonucleotides with 5'-hydroxyl ends eliminated self ligation of the oligonucleotide duplex.

1.) Lys to Ala Substitution

```
                                              (SEQ ID NO: 4)
5' CCG GGT GCA GCA CCT ACT TCA AGT TCT ACA AAG AAA
ACA CAG 3'

(SEQ ID NO: 5)
3' CA CGT CGT GGA TGA AGT TCA AGA TGT TTC TTT TGT
GTC 5'
```

2.) Lys to Arg Substitution

```
                                              (SEQ ID NO: 6)
5' CCG GGT AGG GCG CCA ACT TCA AGT TCT ACA AAG AAA
ACA CAG 3'

(SEQ ID NO: 7)
3' CA TCC CGC GGT TGA AGT TCA AGA TGT TTC TTT TGT
GTC 5'
```

A NarI restriction site (GGCGCC) was also introduced by silent mutation to facilitate screening of recombinant clones.

3.) Deletion of Lys

```
                                              (SEQ ID NO: 8)
5' CCC GGT GCA CCT ACT TCA AGT TCT ACA AAG AAA ACA
CAG 3'

(SEQ ID NO: 9)
3' CA CGT GGA TGA AGT TCA AGA TGT TTC TTT TGT
GTC 5'
```

4.) Lys to Gly Substitution

```
                                              (SEQ ID NO: 10)
5' CCG GGT GGG GCC CCT ACT TCA AGT TCT ACA AAG AAA
ACA CAG 3'
```

```
                                            (SEQ ID NO: 11)
3' CA CCC CGG GGA TGA AGT TCA AGA TGT TTC TTT TGT
GTC 5'
```

An ApaI restriction site (GGGCCC) was also introduced by silent mutation to facilitate screening of recombinant clones.

5.) Lys to Leu Substitution

```
                                            (SEQ ID NO: 12)
5' CCG GGT CTG GCG CCA ACT TCA AGT TCT ACA AAG AAA
ACA CAG 3'

(SEQ ID NO: 13)
3' CA GAC CGC GGT TGA AGT TCA AGA TGT TTC TTT TGT
GTC 5'
```

A NarI restriction site (GGCGCC) was also introduced by silent mutation to facilitate screening of recombinant clones.

6.) Lys to AlaAlaAla Substitution

```
                                            (SEQ ID NO: 14)
5' CCG GGT GCA GCA GCT GCC CCA ACT TCA AGT TCT ACA
AAG AAA ACA CAG 3'

(SEQ ID NO: 15)
3' CA CGT CGT CGA CGG GGT TGA AGT TCA AGA TGT TTC
TTT TGT GTC 5'
```

7.) Lys to Cys Substitution

```
                                            (SEQ ID NO: 16)
5' CCG GGT TGC GCA CCA ACT TCA AGT TCT ACA AAG AAA
ACA CAG 3'

(SEQ ID NO: 17)
3' CA ACG CGT GGT TGA AGT TCA AGA TGT TTC TTT TGT
GTC 5'
```

A FspI restriction site (TGCGCA) was also introduced by silent mutation to facilitate screening of recombinant clones.

8.) Lys to Asp Substitution

```
                                            (SEQ ID NO: 18)
5' CCG GGT GAC GCA CCA ACT TCA AGT TCT ACA AAG AAA
ACA CAG 3'

(SEQ ID NO: 19)
3' CA CTG CGT GGT TGA AGT TCA AGA TGT TTC TTT TGT
GTC 5'
```

The recombinant gene constructs containing the various substitutions or deletion of the Lys codon were confirmed by DNA sequencing.

Example 2

Construction of Antibody-IL-2 Genes Encoding Extra Amino Acid Residues at the Fusion Junction It is common in the art to separate domains in fusion proteins with flexible linkers containing amino acid residues such as glycine and serine. The importance of the spacing between the CH3 and IL-2 was studied in the following mutagenesis experiments. Blunt ended oligonucleotide duplexes encoding different number of amino acid residues were inserted into the SmaI endonuclease restriction site (same recognition site as the XmaI mentioned above) of the huKS-IL-2 expression vector by ligation; and the correct orientation of insertion was confirmed by DNA sequencing. As discussed above, oligonucleotide duplexes with 5'-hydroxyl ends were used to eliminate self ligation.

9.) Lys to Cys Substitution with Linker Ligation

The following linker (oligonucleotide duplex) was inserted into the SmaI endonuclease restriction site of the huKS-IL-2 expression vector by ligation. The sequence GCATGC encodes a SphI restriction site, which facilitated screening of recombinants containing the linker insertion.

```
                    5' G GCA TGC GG 3'

3' C CGT ACG CC 5'
```

After linker ligation into the SmaI site (CCCGGG), the sequence at the fusion junction became

```
C CCG GCA TGC GGG GGT AAA          (SEQ ID NO: 20)
(linker sequence underlined)

Pro Ala Cys Gly Gly Lys          (SEQ ID NO: 21)
```

Therefore, the linker put a Cys residue at the original position of the Lys residue, for a possible interchain disulphide bond formation. The original Lys residue was pushed back by 3 amino acid residues (AlaCysGly).

10.) A Linker Encoding 6 Amino Acid Residues

The following linker (oligonucleotide duplex) was inserted into the SmaI endonuclease restriction site of the huKS-IL-2 expression vector by ligation. The sequence GGATCC encodes a BamHI restriction site, which facilitated screening of recombinants containing the linker insertion.

```
5' G GGT TCA GGA TCC GGA GG 3'      (SEQ ID NO: 22)

3' C CCA AGT CCT AGG CCT CC 5'      (SEQ ID NO: 23)
```

After linker ligation into the SmaI site, the sequence at the fusion junction became ProGlySerGlySerGlyGlyGlyLys (SEQ ID NO: 24), where the six amino acid residues inserted were underlined.

11.) A Linker Encoding 11 Amino Acid Residues

The following linker (oligonucleotide duplex) was inserted into the SmaI endonuclease restriction site of the huKS-IL-2 expression vector by ligation. The sequence GGATCC encodes a BamHI restriction site, which facilitated screening of recombinants containing the linker insertion.

```
                                            (SEQ ID NO: 25)
5' G GGT TCA GGC TCT GGA TCA GGG TCC GGA TCC GG 3'

(SEQ ID NO: 26)
3' C CCA AGT CCG AGA CCT AGT CCC AGG CCT AGG CC 5'
```

After linker ligation into the SmaI site, the sequence at the fusion junction became ProGlySerGlySerGlySerGlySerGlySerGlyGlyLys (SEQ ID NO: 27), where the eleven amino acid residues inserted were underlined.

Example 3

Construction of Antibody-IL-2 Genes with Substitutions of the Pro Codon at the Fusion Junction The proline in the sequence ProGlyLys at the carboxyl terminus of CH3 is mutated to Ala, Leu or Gly, and other amino acids. This is accomplished by replacing a 25 base-pair SapI-SmaI fragment of the KS-IL-2 expression vector by an oligonucleotide duplex encoding the desired change. Each of the following oligonucleotide duplexes has a SapI cohesive end (3-base overhang) and a blunt end (for ligating to the SmaI end of the restriction fragment). The substitutions at the Pro codon are denoted in bold. These substitutions had no significant effect on the pharmacokinetics of the fusion protein, indicating that the structural properties of the Pro residue have no significant effect on the pharmacokinetics of the fusion protein 12.) Pro to Ala Substitution

```
                                          (SEQ ID NO: 28)
5' CG CAG AAG AGC CTC TCC CTG TCC GC 3'

(SEQ ID NO: 29)
3' TC TTC TCG GAG AGG GAC AGG CG 5'
```

13.) Pro to Leu Substitution

```
                                          (SEQ ID NO: 30)
5' CG CAG AAG AGC CTC TCC CTG TCC CT 3'

(SEQ ID NO: 31)
3' TC TTC TCG GAG AGG GAC AGG GA 5'
```

12.) Pro to Gly Substitution

```
                                          (SEQ ID NO: 32)
5' CG CAG AAG AGC CTC TCC CTG TCC GG 3'

(SEQ ID NO: 33)
3' TC TTC TCG GAG AGG GAC AGG CC 5'
```

Example 4

Construction of hu14.18-(Lys to Ala)-IL-2 DNA

In order to show that the effect of the Lys to Ala substitution on the pharmacokinetics of the antibody-IL-2 fusion protein was not limited to the huKS antibody, we chose a different antibody, humanized 14.18 (hu14.18), which recognized GD2, a ganglioside overexpressed on the surface of many human tumor cells. The expression vector for hu14.18-(Lys to Ala)-IL-2 was constructed as described above.

Example 5

Construction of huKS-(Deleted Lys)-TNFα DNA

In order to show that the effect of the Lys residue on the pharmacokinetics of the antibody-IL-2 fusion protein was applicable to other cytokines, we chose a different cytokine, TNFα. The complete cDNA sequence of TNFα was published by Nedwin at al. in Nucleic Acids Res. (1985) 13:6361-6373, and the expression of an antibody-TNFα also has been described by Gillies at al. in *Bioconjugate Chem.* (1993) 4:230-235. The fusion junction of the antibody-TNFα has the sequence SerProGlyLys-ValArgSerSerSer (SEQ ID NO: 34), where Val is the N-terminal residue of the mature TNFα. In order to compare with huKS-TNFα, DNA encoding huKS-(deleted Lys)-TNFα was constructed by an overlapping PCR method [Daugherty at al., (1991) *Nucleic Acids Res.* 19:2471-2476] with mutagenic primers encoding the deletion of the Lys residue. The resultant expression vector for huKS-(deleted Lys)-TNFα therefore encodes the peptide sequence Ser-ProGly-ValArgSerSerSer (SEQ ID NO: 35) at the fusion junction. Additional modifications of this fusion protein according to the new invention might include the removal of the Arg residue in the amino terminal sequence of TNF to further reduce the overall charge of the junction region.

Example 6

Construction of huKS-(EU)-(Lys to Ala)-IL-2 DNA

All the antibody-cytokine fusion proteins mentioned in the examples above were based on a certain allotype of the human IgG1 represented by the myeloma H chain, KOL. In order to show that the effect of the Lys to Ala substitution on the pharmacokinetics of the antibody-IL-2 fusion protein was not limited to KOL, we chose a different IgG1 allotype represented by the myeloma H chain, EU. The EU allotype differs from the KOL allotype in three amino acid residues in the constant regions. The EU allotype contains Lys-229 at the end of CH1, and Asp-356 and Leu-358 at the beginning of CH3. The KOL allotype contains Arg-229, Glu-356 and Met-358 at the corresponding positions. The DNA encoding the EU allotype was obtained by mutagenesis of the KOL DNA using the overlapping PCR method. The resultant EU DNA was then used to replace the corresponding fragment of the KOL DNA to generate the expression vector for producing huKS-(EU)-(Lys to Ala)-IL-2.

Example 7

Transfection of Cells and Expression of Proteins

For transient transfection, the plasmid was introduced into Baby Hamster Kidney (BHK) cells by lipofection using Lipofectamine Plus (Life Technologies, Gaithersburg, Md.) according to supplier's protocol.

In order to obtain stably transfected clones, plasmid DNA was introduced into the mouse myeloma NS/0 cells by electroporation. NS/0 cells were grown in Dulbecco's modified Eagle's medium supplemented with 10% fetal bovine serum, 2 mM glutamine and penicillin/streptomycin. About $5 \times 10^6$ cells were washed once with PBS and resuspended in 0.5 ml PBS. Ten μg of linearized plasmid DNA were then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min. on ice, after which they were resuspended in growth medium and then plated onto two 96 well plates. Stably transfected clones were selected by growth in the presence of 100 nM methotrexate (MTX), which was introduced two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX.

For routine characterization by gel electrophoresis, antibody-cytokine fusion proteins in the conditioned media were captured on Protein A Sepharose (Repligen, Cambridge, Mass.) and then eluted by boiling in the protein sample buffer with or without 2-mercaptoethanol. After electrophoresis on an SDS gel, the protein bands were visualized by Coomassie staining. The antibody heavy chain-IL-2 and the light chain had apparent MW of about 67 and 28 kD respectively, on SDS-PAGE.

For purification, the fusion proteins bound on Protein A Sepharose were eluted in a sodium phosphate buffer (100 mM $NaH_2PO_4$, pH 3, and 150 mM NaCl). The eluate was then immediately neutralized with 0.1N NaOH.

Example 8

ELISA Procedures

Figure 1B:
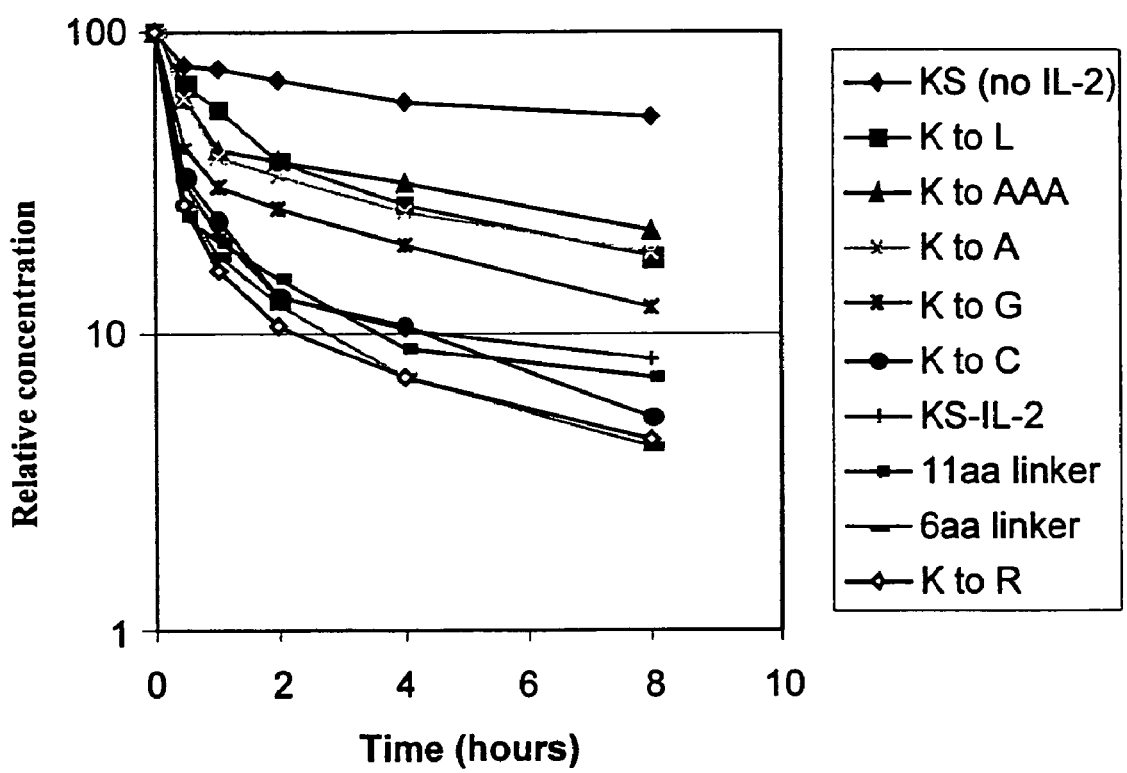

ELISAs were used to determine the concentrations of protein products in the supernatants of MTX-resistant clones and other test samples. The anti-huFc ELISA consists of a capturing step using goat anti-human IgG (against both heavy and light chains) and a detection step using the horseradish peroxidase-conjugated F(ab')$_2$ fragment of goat anti-human IgG, Fc fragment specific. Therefore, the anti-huFc ELISA measures human IgG, either as an antibody by itself or as a cytokine fusion protein. To determine the concentration of the intact antibody-IL-2 fusion protein, an IL-2-detection ELISA was used. It consists of the same capturing step using goat anti-human IgG (against both heavy and light chains), but the detection step uses a detection antibody directed against IL-2. In some experiments, EPCAM was used instead of a capture antibody to detect KS-IL-2 fusion proteins, since the KS antibody recognizes EPCAM. In some experiments, a commercial human IL-2 ELISA detection kit was used (R&D Systems). All the different ELISA procedures involving IL-2 detection antibodies gave similar results. However, as can be seen from a comparison of FIG. 1A and FIG. 1B, there is a progressive loss of IL-2-immunoreactive material compared to human Fc immunoreactive material in later pharmacokinetic time points. This effect is most pronounced for fusion proteins that have the poorest pharmacokinetic properties.

The anti-huFc ELISA is described in detail below.

A. Coating Plates.

ELISA plates were coated with AffiniPure Goat anti-Human IgG (H+L) (Jackson Immuno Research Laboratories, West Grove, Pa.) at 5 µg/mL in PBS, and 100 µL/well in 96-well plates (Nunc-Immuno plate Maxisorp). Coated plates were covered and incubated at 4° C. overnight. Plates were then washed 4 times with 0.05% Tween (Tween 20) in PBS, and blocked with 1% BSA/1% goat serum in PBS, 200 µL/well. After incubation with the blocking buffer at 37° C. for 2 hrs, the plates were washed 4 times with 0.05% Tween in PBS and tapped dry on paper towels.

B. Incubation with Test Samples and Secondary Antibody

Test samples were diluted to the proper concentrations in sample buffer, which contains 1% BSA/1% goat serum/ 0.05% Tween in PBS. A standard curve was prepared with a chimeric antibody (with a human Fc), the concentration of which was known. To prepare a standard curve, serial dilutions are made in the sample buffer to give a standard curve ranging from 125 ng/mL to 3.9 ng/mL. The diluted samples and standards were added to the plate, 100 µL/well and the plate was incubated at 37° C. for 2 hr. After incubation, the plate was washed 8 times with 0.05% Tween in PBS. To each well was then added 100 µL of the secondary antibody, the horseradish peroxidase-conjugated AffiniPure F(ab')$_2$ fragment goat anti-human IgG, Fc fragment specific (Jackson Immuno Research), diluted around 1:120,000 in the sample buffer. The exact dilution of the secondary antibody has to be determined for each lot of the HRP-conjugated anti-human IgG. After incubation at 37° C. for 2 hr, the plate was washed 8 times with 0.05% Tween in PBS.

C. Development

The substrate solution was added to the plate at 100 µL/well. The substrate solution was prepared by dissolving 30 mg of OPD (o-phenylenediamine dihydrochloride, 1 tablet) into 15 mL of 0.025 M Citric acid/0.05 M $Na_2HPO_4$ buffer, pH 5, which contained 0.03% of freshly added $H_2O_2$. The color was allowed to develop for 30 min. at room temperature in the dark. The developing time is subject to change, depending on lot to lot variability of the coated plates, the secondary antibody, etc. Watch the color development in the standard curve to determine when to stop the reaction. The reaction was stopped by adding 4N $H_2SO_4$, 100 µL/well. The plate was read by a plate reader, which was set at both 490 and 650 nm and programmed to subtract the background OD at 650 nm from the OD at 490 nm.

Example 9

Pharmacokinetic Behavior of Antibody-Cytokine Fusion Proteins Carrying Alterations at the Fusion Junction The fusion proteins were tested for their pharmacokinetic behavior following intravenous injection into Balb/c mice. Blood was collected from mice by retro-orbital bleeding and stored at 4° C. in Eppendorf micro-centrifuge tubes. In some cases, two different ELISA methods were used to measure both the amount of human antibody and the amount of second, fused non-Ig protein remaining in the blood at various time points. Alternatively, the presence of the non-Ig moiety was inferred by Western blot analysis of pharmacokinetic time points.

Figure 2:
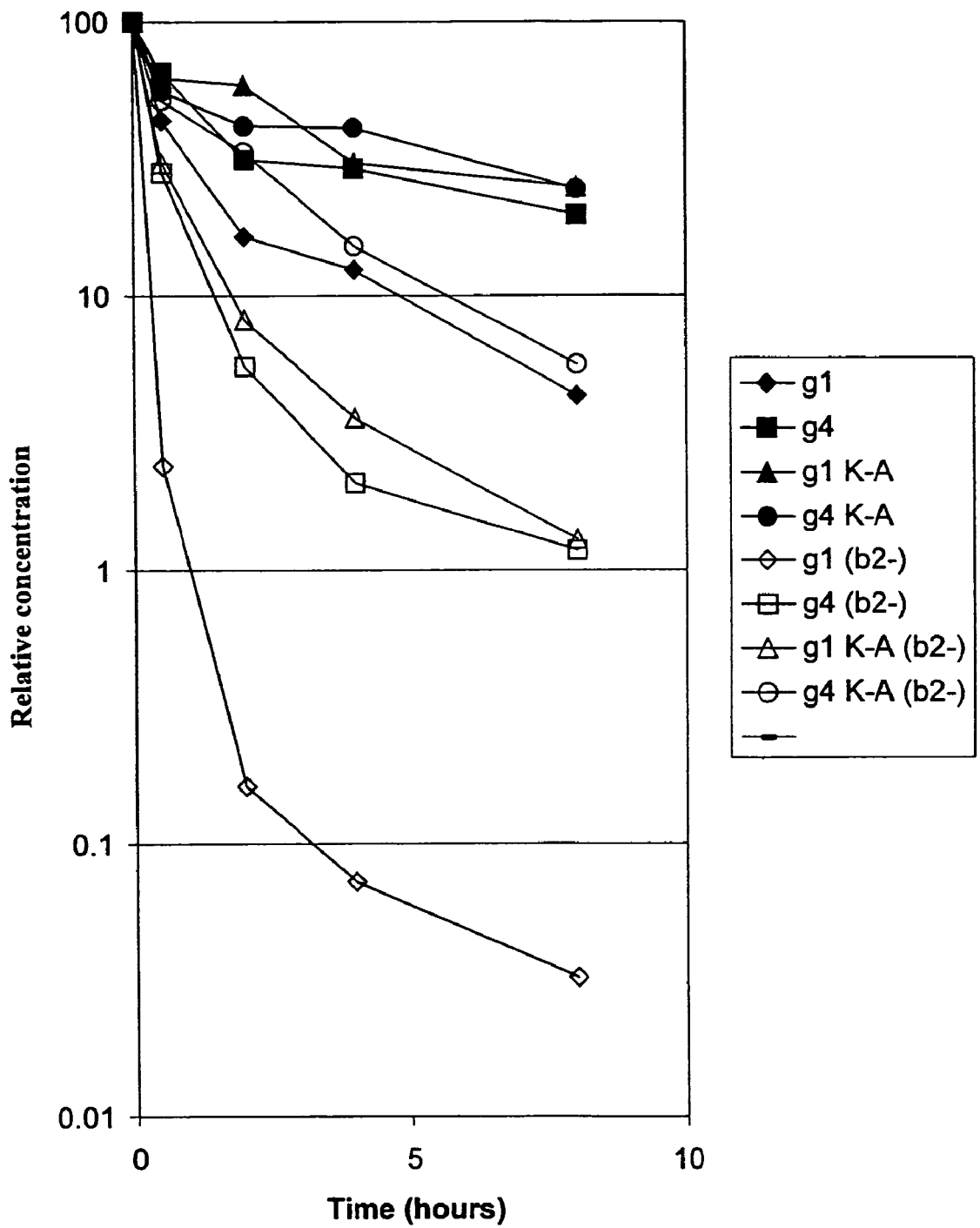
FIG. 2 shows the pharmacokinetic properties of KS-IL-2 fusion proteins carrying either the gamma1 or gamma4 chain with either the wild-type lysine or the lysine-to-alanine mutation at the C-terminus of the antibody heavy chain. Levels of antibody or fusion protein were measured by an ELISA that tests for the IL-2 moiety.

Using the techniques described in the preceding examples, the KS(gamma1)-IL-2 fusion mutant proteins were injected into mice, and the effect on serum half-life was determined. Some of the results are shown in FIG. 1 and FIG. 2. In addition, the effect of deletion of the antibody heavy chain's C-terminal lysine was examined in an IgG(gamma1)-IL-2 fusion in which the antibody had a different binding specificity. The pharmacokinetic properties of a 14.18(Lys→Ala)-IL-2 were superior to 14.18-IL-2 to an extent that was similar to the improvement of KS(Lys→Ala)-IL-2 as compared to KS-IL-2.

For antibody-IL-2 fusions, the ranking of the effect of mutations affecting the C-terminal lysine of the heavy chain on the pharmacokinetic properties was (from best to worst): Lys→Leu~Lys→Ala~Lys→Ala$_3$>Lys→(deleted)>Lys→ Asp~Lys→Gly>Lys→(no change)~Lys→Cys>Lys→Arg.

Figure 3:
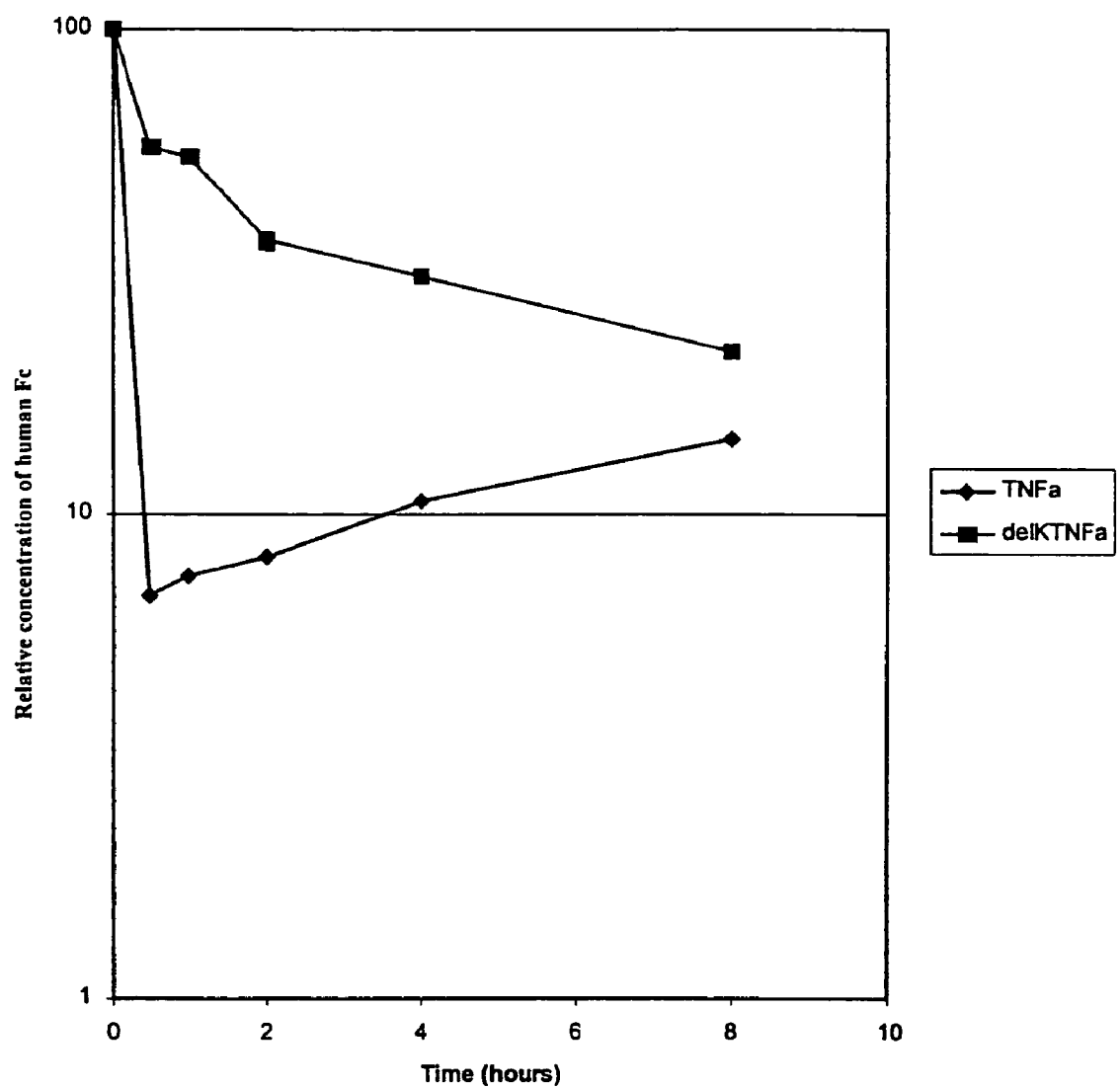
FIG. 3 shows the pharmacokinetic properties of fusions of a human antibody to Tumor Necrosis Factor alpha (TNFalpha). Levels of fusion protein were measured by an ELISA that tests for the human Fc region. Shown are the levels of an intact antibody-TNFalpha fusion protein (black diamonds) and the levels of an otherwise identical fusion protein in which the C-terminal lysine of the antibody moiety has been deleted (gray squares).
Figure 4:
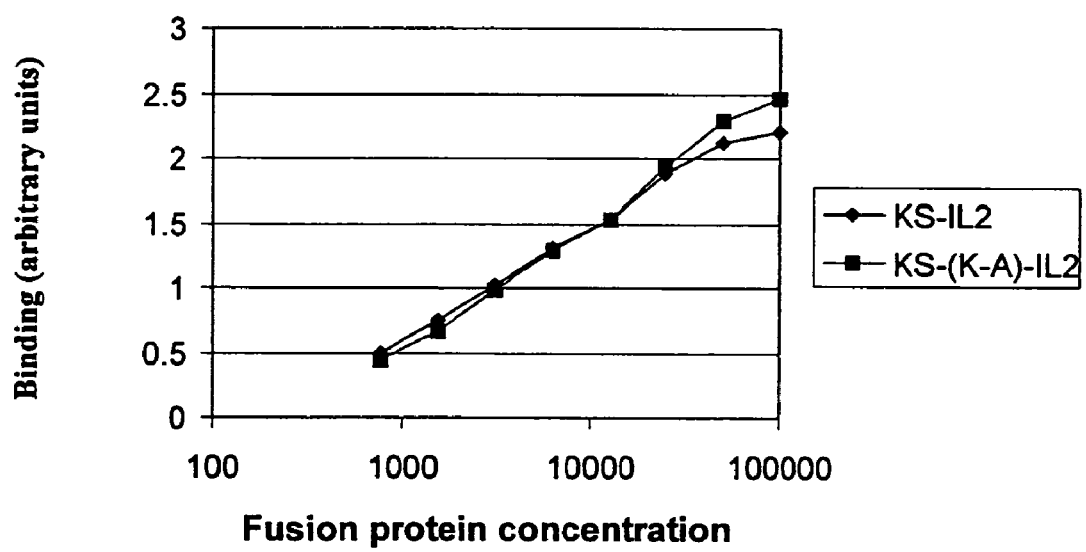
FIG. 4 shows the binding of antibody-IL-2 fusion proteins to membranes of fixed J774 cells, which are rich in the FcγR class of receptor. Shown are the binding of a non-mutant KS-IL-12 fusion protein (black diamonds) and a KS-IL-12 fusion protein carrying a mutation of the heavy chain C-terminal Lysine to Alanine (gray squares).

The pharmacokinetic properties of KS(Lys→deleted)-TNFalpha were significantly improved as compared to KS-TNFalpha (FIG. 3). The pharmacokinetic profile of the KS-TNFalpha fusion protein was unusual in that, when the levels of human antibody are measured by Fc ELISA, there was a sharp drop in the level of detected protein within the first 30 minutes, followed by a slow increase in the level of human Fc-reactive material. This effect was highly reproducible.

When pharmacokinetic samples were analyzed by Western blotting, it was found that human Fc-cross-reactive material was in the form of intact antibody; the TNF moiety had been cleaved off and lost. However, similar analysis of the KS-TNFalpha fusion protein carrying a deletion of the C-terminal lysine indicated that this protein survived primarily in an intact form, with TNF still present.

Figure 5:
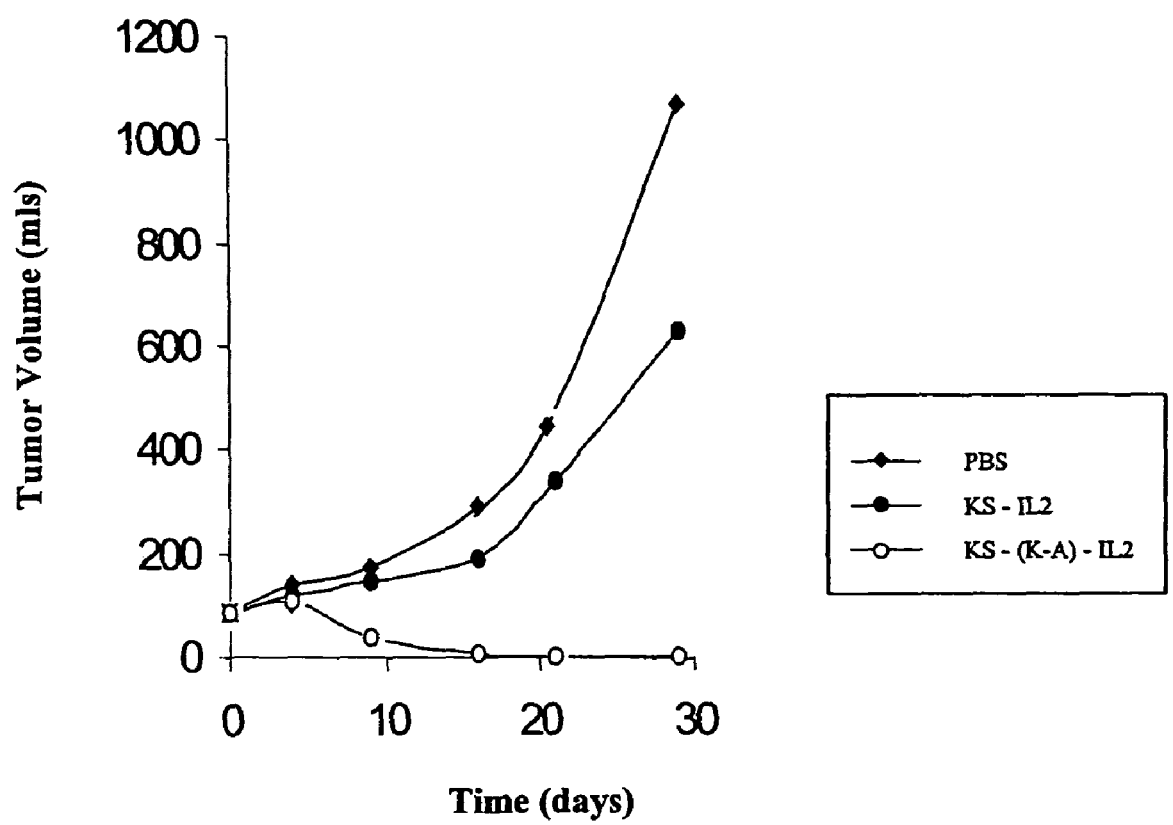
FIG. 5 shows the effect of antibody-cytokine fusion protein treatment of Balb/C mice bearing subcutaneous tumors derived from CT26 colon carcinoma cells that were engineered to express human EpCAM, the antigen for KS.

In addition, a KS-TNFalpha fusion protein was expressed in which the first eight amino acids of the mature TNFalpha sequence were deleted. The pharmacokinetic properties of the deleted KS-TNFalpha fusion protein were superior to corresponding proteins having the entire mature TNF sequence. This is likely due to removal of the charged Arg residue at the +2 position of the mature TNF which increases the hydrophobicity of the junctional region.

Changing the heavy chain constant regions of KS(Lys→Ala)-IL-2 and KS-IL-2 from KOL to EU had no effect on the pharmacokinetic properties of either protein.

Taken together, these results indicate that mutation of the junction caused a significant improvement of the pharmacokinetic properties of Ig fusion proteins. The effect was seen with diverse antibodies, and diverse non-Ig proteins fused to an Ig moiety.

Example 10

Combining Mutations at the Fusion Junction with a Change in Ig Type from Gamma1 to Gamma4 Leads to a Synergistic Enhancement of Serum Half-Life that is Independent of FcRp Function The human gamma4 Fc region binds poorly to Fc receptors. As a result, fusion proteins that comprise a gamma4 Fc region generally have a superior pharmacokinetic properties as compared to fusion proteins having the gamma1 chain. To address whether junction mutations affect pharmacokinetics through an effect on an Fc receptor interaction, an FcRp interaction, or both, the pharmacokinetic properties of gamma1- and gamma4-containing fusion proteins with or without junction mutations were examined in mice that were either normal or defective in FcRp. The results of these pharmacokinetic experiments are shown in FIG. 2.

FIG. 2 shows the pharmacokinetic behavior of a KS(gamma1)-IL-2 fusion protein, a KS(gamma4)-IL-2 fusion protein, a KS(gamma1)(Lys-to-Ala)-IL-2 fusion protein, and a KS(gamma4)(Lys-to-Ala)-IL-2 fusion protein. Normal mice and mutant mice defective in beta2 microglobulin were examined.

These data indicated that, in a normal mouse, the pharmacokinetics of an IgG-gamma1 antibody-IL-2 fusion protein were improved by introducing a Lys-to-Ala mutation at the C-terminus of the antibody moiety. Similarly, the pharmacokinetics of an IgG-gamma4 antibody-IL-2 fusion protein were improved by introducing a Lys-to-Ala mutation at the C-terminus of the antibody moiety. These data indicate that a junction mutation can improve the pharmacokinetic properties of a fusion protein that already has improved pharmacokinetics as a result of reduced Fc receptor binding.

FIG. 2 also shows the pharmacokinetic properties of the same proteins when injected into mutant mice lacking the beta2-microglobulin protein, which is an essential subunit of FcRp (Junghans and Anderson, *Proc. Nat Acad. Sci*. (1996) 93:5512-5516). Thus, these mutant mice are defective in FcRp activity. As a result, the catabolism of antibodies is about 10-fold faster in such mutant mice than in normal mice.

The data of FIG. 2 indicated that the KS (gamma1) antibody, a KS (gamma1)-IL-2 fusion protein, a KS (gamma4)-IL-2 fusion protein, a KS (gamma1)(Lys-to-Ala)-IL-2 fusion protein, and a KS (gamma4)(Lys-to-Ala)-IL-2 fusion protein all were catabolized more rapidly in the beta2-microglobulin mutant mice than in wild-type mice. However, the relative order of serum half-lives is the same for these proteins in both mouse strains: the unfused antibody has the best pharmacokinetics, followed by the KS(gamma4)(Lys-to-Ala)-IL-2 fusion protein, the KS(gamma1)(Lys-to-Ala)-IL-2 fusion protein, the KS(gamma4)-IL-2 fusion protein, with the KS(gamma1)-IL-2 fusion protein having the worst pharmacokinetic properties. If a junction mutation had its effect exclusively by changing the interaction of a fusion protein with FcRp, then in the absence of FcRp function, the junction mutation should have no effect on pharmacokinetics.

Example 11

Mutation of the Junction Region in an Intact Antibody has No Effect on Serum Half Life A mutation in a gene encoding the heavy chain of the intact, unfused KS antibody is engineered to change the C-terminal lysine to an alanine. The wild-type and mutant forms of KS are expressed and purified by the methods described above, and the pharmacokinetic properties are compared. The pharmacokinetic behaviors of the wild-type and mutant antibodies are found to be indistinguishable.

Example 12

Binding to Fc Receptor by Antibody Fusion Proteins with or without Mutations at the Fusion Junction Using a standard procedure, the binding of KS-IL-2 and KS(K-A)-IL-2 to Fc receptors was examined. No effect of the mutation was found. Fusion proteins were expressed and purified as described above, and were tested for their ability to bind to fixed J774 cells, which express the Fc receptor. Results are shown in FIG. 4.

Example 13

Treatment of Colon Carcinoma in a Mammal with an Antibody-Cytokine Fusion Protein Containing a Junction Mutation To test whether a cytokine-antibody fusion protein with a junction mutation would be advantageous in treatment of colon carcinoma in a mammal, the following experiments were performed. CT26 is a colon carcinoma cell line derived from Balb/C mice. By standard genetic engineering techniques, this cell line was engineered to express the human epithelial cell adhesion molecule (EpCAM), which is the antigen recognized by the KS antibody; these cells are termed CT26/EpCAM cells (Gillies at al. *Journal of Immunology* (1998) 160:6195-6203).

Balb/C mice were subcutaneously inoculated with $2\times10^6$ CT26/EpCAM cells. When tumors reached a volume of about 50-200 cubic millimeters, mice were randomized into three groups of 7 mice for further study. Beginning at day 0, tumor-bearing mice were treated with PBS, about 10 micrograms of KS-IL2 with an IgG1 heavy chain (KS-IL2gamma1), or about 10 micrograms of KS-IL2 with an IgG1 heavy chain and the Lys to Ala mutation described in the previous examples (KS-IL2gamma1 [Lys to Ala]). Mice were injected intravenously, once per day for five days. Tumor sizes were measured with calipers.

The results of one such experiment are shown in FIG. 5. In this experiment, KS-IL2gamma1 caused a significant decrease in the volume of many, but not all tumors. In six of the seven KS-IL2gamma1-treated animals, tumors were still measurable on day 21. However, in the KS-IL2gamma1 (Lys to Ala)-treated animals, the tumors shrank, so that by day 21, the tumors in all seven animals were unmeasurable, and by day 16, only two of seven mice had measurable tumors. In FIG. 5, black diamonds indicate average tumor volumes in mice that were injected with PBS as controls on days 0, 1, 2, 3, and 4. Filled circles indicate average tumor volumes in mice treated with 10 micrograms of KS-IL2 gamma1. Intravenous injections were performed. The x-axis indicates the number of days elapsed following the first injection; the y-axis indicates the average tumor volume in cubic milliliters.

Example 14

Inhibition of Metastasis in a Mammal Treated with an Antibody-Cytokine Fusion Protein Containing a Junction Mutation To test whether an antibody-cytokine fusion protein could inhibit metastatic growth of tumor cells, the following experiments were performed. Lewis Lung Carcinoma (LLC) is a lung carcinoma cell line derived from C57/B16 mice. By standard genetic engineering techniques, this cell line was engineered to express the human epithelial cell adhesion molecule (EpCAM), which is the antigen recognized by the KS antibody; these cells are termed LLC/EpCAM cells.

C57/B16 mice were intravenously injected with $1\times10^6$ LLC/EpCAM cells. After five days, mice were randomized into three groups of 6 mice and treated with either PBS, about 20 micrograms of KS-IL2, or about 20 micrograms of KS-Ala-IL2 (KS-IL2 with a Lys to Ala change at the C-terminus of the Ig moiety). Metastases were quantitated on day 24. As indicated in the table below, the PBS-treated group had large numbers of metastases into the lungs. Animals treated with KS-γ1-IL2 had a significantly reduced number of metastases. However, animals treated with KS-γ1-ala-IL2 had even fewer metastases than animals treated with KS-γ1-IL2, and in one animal, no metastases at all were detected.

| Treatment Group | Number of Metastases | Lung Wt. (g) |
| --- | --- | --- |
| PBS | >250, >250, >250, >250, >250, >250 | 0.92 +/− 0.14 |
| KS-γ1-IL2 | 62, 37, 18, 17, 11, 9 | 0.27 +/− 0.04 |
| KS-γ1-ala-IL2 | 4, 4, 3, 3, 1, 0 | 0.25 +/− 0.02 |

Taken together, Examples 13 and 14 illustrate that antibody-cytokine fusion proteins can inhibit establishment of metastases as well as growth of tumor cells at the primary site. In addition, the results indicate that antibody-cytokine fusion proteins can inhibit disease resulting from a variety of different tumor types, such as colon cancer and lung cancer. Furthermore, antibody-cytokine fusion proteins with at least one amino acid change in the linker region in accordance with the invention are more effective at inhibiting metastases and tumor growth that antibody-cytokine fusion proteins with no amino acid change in the linker region.

Example 15

Assay of Antibody Fusion Proteins with Junction Mutations for Resistance to Proteases To address whether antibody-cytokine fusion proteins with junction mutations were more or less sensitive to protease digestion, purified KS-IL2 and KS-Ala-IL2 were treated with various proteases for various times, and the resulting products were analyzed by SDS-PAGE.

In one experiment, 4 micrograms of KS-IL2 and KS-Ala-IL2 were treated with 0.1 mU or 0.4 mU of Cathepsin D (Enzyme Systems, Livermore, Calif.) for about 16 hours at 37 degrees C. and analyzed by SDS-PAGE. Buffer conditions were used according to the manufacturer's instructions. When KS-IL2 was treated with 0.4 mU of Cathepsin D, about 50% of the KS-IL2 heavy chain was converted to various lower molecular weight forms. The dominant digestion product had a molecular weight slightly less than that of KS-IL2 heavy chain, but much larger than the KS heavy chain. This result indicates that most of the cleavage by Cathepsin D was not taking place at the heavy chain-IL2 junction.

In contrast, when KS-Ala-IL2 was incubated with 0.4 mU of Cathepsin D under the same conditions, the extent of cleavage by Cathepsin D was much less, and a band with the molecular weight of the major KS-IL2 degradation product was essentially undetectable.

In a second experiment, 4 micrograms of KS-IL2 and KS-Ala-IL2 were treated with 25 mU or 50 mU of Cathepsin L (Enzyme Systems, Livermore, Calif.) for about 16 hours at 37 degrees C. and analyzed by SDS-PAGE. Buffer conditions were used according to the manufacturer's instructions. When KS-IL2 was treated with 50 mU of Cathepsin L, almost all of the KS-IL2 heavy chain was converted to various lower molecular weight forms. The dominant digestion product had a molecular weight about the same as the KS heavy chain. This result indicates that much of the cleavage by Cathepsin L was taking place near or at the heavy chain-IL2 junction.

In contrast, when KS-Ala-IL2 was incubated with 50 mU of Cathepsin L under the same conditions, the extent of cleavage by Cathepsin L was much less, and a band with the molecular weight of the major KS-IL2 degradation product was still the major molecular weight species observed.

In a third experiment, 4 micrograms of KS-IL2 and KS-Ala-IL2 were treated with 0.04 mU, 0.1 mU or 0.2 mU of plasmin (Sigma, St. Louis, Minn.) for about 16 hours at 37 degrees C. and analyzed by SDS-PAGE. Buffer conditions were used according to the manufacturer's instructions. When KS-IL2 was treated with 0.04 mU of plasmin, about ¾ of the KS-IL2 heavy chain was converted to a lower molecular weight form with an apparent molecular weight about 30 amino acids greater than that of the KS heavy chain. When KS-IL2 was treated with 0.2 mU of plasmin, essentially all of the KS-IL2 heavy chain was converted to a lower molecular weight form with an apparent molecular weight about 30 amino acids greater than that of the KS heavy chain. These results indicate that the cleavage of KS-IL2 by plasmin was taking place close to, but not at the heavy chain-IL2 junction.

In contrast, when KS-Ala-IL2 was incubated with 0.04 mU of plasmin under the same conditions, the extent of cleavage by plasmin was barely detectable. When KS-Ala-IL2 was incubated with 0.2 mU of plasmin, some uncleaved product was detected. In addition when KS-Ala-IL2 was cleaved with plasmin, a species with a molecular size about 90 amino acids greater than the KS-IL2 heavy chain accumulated to a significant extent; in the KS-IL2 digestions by plasmin, this +90 species was probably rapidly cleaved to the lower molecular weight +30 species, and thus failed to accumulate. Nonetheless, the Lys-to-Ala mutation caused a significant stabilization of intact KS-IL2 in the presence of plasmin. In each case, the antibody light chain was uncleaved under the conditions used.

Taken together, these results indicated that the Lys-to-Ala mutation caused a general resistance to protease cleavage, even to cleavages that do not take place at the site of the mutation. Without wishing to be bound by any particular theory, the Lys-to-Ala mutation may cause the IL-2 moiety of KS to become more resistant to proteases. Proteases may play an important role in the pharmacokinetic properties of antibody fusion proteins. For example, when antibody fusion proteins are taken up by cells bearing an Fc receptor and transported into the early endosome, it may be that the antibody moiety is resistant to the proteolytic conditions used, but that the fusion partner moiety is more sensitive, resulting in partial or complete digestion of the antibody fusion protein.

Example 16

Use of Protease Digestion to Evaluate Mutations in Antibody Fusion Proteins

This example provides a general method for improving the pharmacokinetic properties of a protein. A protein is tested for its pharmacokinetic properties and also its sensitivity to proteases. Variant proteins are generated and tested for greater resistance to proteolysis. Those variants with enhanced resistance to proteolysis are then tested for their pharmacokinetic properties. It is found that the proportion of proteolysis-resistant proteins with improved pharmacokinetic properties is greater than for the population of variant proteins as a whole. Some variant proteins with improved pharmacokinetic properties have one or more amino acid substitutions that do not cause a profound change in the protein structure that can be inferred by inspection of the encoding sequence, such as introduction of an N-linked glycosylation site.

Variant proteins are generated by, for example, mutagenesis of an expression construct and isolation of clones expressing individual variant proteins. Any of a variety of mutagenesis techniques is used, including site-directed mutagenesis, random mutagenesis, PCR-mutagenesis, and mutagenesis techniques that generate hybrid sequences from related genes.

It is useful to use intracellular proteases, such as endosomal proteases, for these assays. Without wishing to be bound by any particular theory, it is believed that the pharmacokinetics of certain proteins, particularly proteins that are not removed by renal filtration, is determined by proteolysis that occurs upon endocytosis.

It is also useful to use extracellular proteases, such as trypsin, chymotrypsin, plasmin, other digestive protease, other serum proteases such as clotting factors, and tissue-specific proteases. For example, tumor-specific proteases are used to test variant proteins and identify those variants that have improved pharmacokinetic properties and stability within the tumor microenvironment. In another example, proteins that are to be orally delivered are tested for their resistance to enzymes present in the gastro-intestinal tract, such as trypsin and chymotrypsin. It is found that variant proteins with enhanced resistance to gastro-intestinal enzymes have improved pharmacokinetic properties, such as a greater AUC (Area Under the Curve).

For example, an expression construct encoding a fusion protein containing part or all of an antibody is mutagenized. Clones are generated, the corresponding proteins are expressed, and the proteins are tested, either individually or in small pools, for relative sensitivity to proteases. Variant antibody fusion proteins with enhanced resistance to proteases are then tested for their pharmacokinetic properties, and a significant number of the protease-resistant antibody fusion protein variants have improved pharmacokinetic properties. The nucleic acids encoding the improved variant fusion proteins are sequenced, and some improved variants are found to contain mutations at sites other than the fusion protein junction that cause the phenotype of enhanced resistance to proteolysis and improved pharmacokinetics.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

Each of the patent documents and scientific publications disclosed herein is incorporated by reference into this application in its entirety.

What is claimed is:

1. A method for increasing the circulating half-life of an antibody-based fusion protein having an immunoglobulin (Ig) chain linked to a non-Ig protein via a junction point, the method comprising expressing the antibody-based fusion protein as an N-terminal Ig chain linked to a C-terminal non-Ig protein, the Ig chain comprising an IgG2, IgG3, IgG4, IgA, IgM, IgD, or IgE constant domain and an amino acid substitution introducing a hydrophobic or non-polar amino acid within 10 amino acids from the C-terminus of the Ig chain.

2. The method of claim 1, wherein the constant domain comprises at least one of a CH1, CH2, or CH3 domain.

3. The method of claim 1, wherein the constant domain comprises at least one of a CH2 or CH3 domain.

4. The method of claim 1, wherein said amino acid substitution increases the hydrophobicity of said antibody-based fusion protein.

5. The method of claim 1, wherein said substitution replaces a charged amino acid with a hydrophobic or nonpolar amino acid.

6. The method of claim 1, wherein said substitution changes the C-terminal amino acid of the Ig chain.

7. The method of claim 6, wherein the Ig chain comprises the CH2 domain of the IgG2 constant region and a C-terminal lysine is substituted with a non-polar or hydrophobic amino acid.

8. The method of claim 7, wherein the C-terminal lysine is substituted with an alanine.

9. The method of claim 7, wherein the non-Ig protein is a cytokine.

10. The method of claim 1, wherein the Ig chain comprises part of an Ig heavy chain.

11. The method of claim 10, wherein said part of an Ig heavy chain further has binding affinity for an immunoglobulin protection receptor.

12. The method of claim 10, wherein said Ig chain has substantially reduced binding affinity for a Fc receptor selected from the group consisting of FcγRI, FcγRII and FcγRIII, when compared to the binding affinity of an unsubstituted Ig chain for said Fc receptor.

13. The method of claim 1, wherein the Ig chain comprises at least the CH2 domain of an IgG2 or an IgG4 constant region.

14. The method of claim 1, further comprising a linker between said Ig chain and said non-Ig protein.

15. The method of claim 1, wherein said hydrophobic or non-polar amino acid is selected from the group consisting of Leu, Trp, Ala, and Gly.

16. The method of claim 15, wherein said hydrophobic or non-polar amino acid is selected from the group consisting of Trp, Ala, and Gly.

17. The method of claim 1, wherein said non-Ig protein is a secreted protein.

18. The method of claim 17, wherein said non-Ig protein is a mature form of said secreted protein.

19. The method of claim 1, wherein said non-Ig protein is interleukin-2.

20. A method for increasing the circulating half-life of an antibody-based fusion protein having an immunoglobulin (Ig) chain linked to a non-Ig protein via a junction point, the method comprising expressing the antibody-based fusion protein as an N-terminal Ig chain linked to a C-terminal non-Ig protein, the Ig chain comprising: at least one of a CH2 and CH3 domain; and an amino acid sequence that is non-natural within 10 amino acids from its C-terminus, the non-natural amino acid sequence comprising an amino acid substitution introducing a hydrophobic or non-polar amino acid.

21. The method of claim 20, wherein the Ig chain is an IgG1, IgG2, IgG3, IgG4, IgA, IgM, IgD, or IgE chain.

22. The method of claim 20, wherein said amino acid substitution increases the hydrophobicity of said antibody-based fusion protein.

23. The method of claim 20, wherein said amino acid substitution replaces a charged amino acid with a hydrophobic or non-polar amino acid.

24. The method of claim 20, wherein said substitution changes the C-terminal amino acid of the Ig chain.

25. The method of claim 24, wherein the Ig chain comprises the CH2 domain of the IgG2 constant region and a C-terminal lysine is substituted with a nonpolar or hydrophobic amino acid.

26. The method of claim 25, wherein the C-terminal lysine is substituted with an alanine.

27. The method of claim 25, wherein the non-Ig protein is a cytokine.

28. The method of claim 20, wherein the Ig chain comprises at least the CH2 domain of an IgG2 or an IgG4 constant region.

29. The method of claim 20, further comprising a linker between said Ig chain and said non-Ig protein.

30. The method of claim 20, wherein said hydrophobic or non-polar amino acid is selected from the group consisting of Leu, Trp, Ala, and Gly.

31. The method of claim 30, wherein said hydrophobic or non-polar amino acid is selected from the group consisting of Trp, Ala, and Gly.

32. A method for increasing the circulating half-life of an antibody-based fusion protein having an immunoglobulin (Ig) chain linked to a non-Ig protein via a junction point, the method comprising expressing the antibody-based fusion protein as an N-terminal immunoglobulin (Ig) chain linked to a C-terminal non-Ig protein, the Ig chain comprising an amino acid substitution within 10 amino acids from the C-terminus, the substitution replacing a charged amino acid with a hydrophobic or non-polar amino acid.

33. The method of claim 32, wherein said hydrophobic or non-polar amino acid is selected from the group consisting of Leu, Trp, Ala, and Gly.

34. The method of claim 33, wherein said hydrophobic or non-polar amino acid is selected from the group consisting of Trp, Ala, and Gly.

35. A method for increasing the circulating half-life of an antibody-based fusion protein having an immunoglobulin (Ig) chain linked to a non-Ig protein via a junction point, the method comprising expressing the antibody-based fusion protein as an N-terminal immunoglobulin (Ig) chain linked to a C-terminal non-Ig protein, the N-terminal Ig chain comprising an amino acid substitution within 10 amino acids from the C-terminus of the Ig chain, the substitution introducing a hydrophobic or non-polar amino acid selected from the group consisting of Ala, Gly and Trp.

36. A method for increasing the circulating half-life of an antibody-based fusion protein having an immunoglobulin (Ig) chain linked to a non-Ig protein via a junction point, the method comprising expressing the antibody-based fusion protein as an N-terminal Ig chain linked to a C-terminal non-Ig protein, the C-terminal non-Ig protein comprising an amino acid substitution introducing a hydrophobic or non-polar amino acid within 10 amino acids of the N-terminus of the C-terminal non-Ig protein.

37. The method of claim 36, wherein said amino acid substitution increases the hydrophobicity of said antibody-based fusion protein.

38. The method of claim 36, wherein the Ig chain comprises (i) a deletion of a charged an amino acid within 10 amino acids of the C-terminus of the Ig chain, or (ii) an amino acid alteration introducing a hydrophobic or non-polar amino acid within 10 amino acids of the C-terminus of the Ig chain.

39. The method of claim 36, wherein the hydrophobic or non-polar amino acid is Ala.

40. The method of claim 36, further comprising a linker between said Ig chain and said non-Ig protein.

41. The method of claim 36, wherein said hydrophobic or non-polar amino acid is selected from the group consisting of Leu, Trp, Ala, and Gly.

42. A method for increasing the circulating half-life of an antibody-based fusion protein having an immunoglobulin (Ig) chain linked to a non-Ig protein via a junction point, the method comprising expressing the antibody-based fusion protein as an N-terminal immunoglobulin (Ig) chain linked to a C-terminal non-Ig protein, the Ig chain comprising at least one of a CH2 and a CH3 domain, and the C-terminal non-Ig protein comprising an amino acid alteration within 10 amino acids of the N-terminus of the C-terminal non-Ig protein, the alteration introducing an amino acid selected from the group consisting of Leu and Trp.

* * * * *

UNITED STATES PATENT AND TRADEMARK OFFICE
CERTIFICATE OF CORRECTION

PATENT NO. : 7,790,415 B2  
APPLICATION NO. : 12/360682  
DATED : September 7, 2010  
INVENTOR(S) : Stephen D. Gillies et al.

It is certified that error appears in the above-identified patent and that said Letters Patent is hereby corrected as shown below:

In Claim 38, column 36, line 30, delete "a charged."

Signed and Sealed this

Thirtieth Day of November, 2010

David J. Kappos  
*Director of the United States Patent and Trademark Office*

SEQUENCE LISTING

<160> NUMBER OF SEQ ID NOS: 35

<210> SEQ ID NO 1
<211> LENGTH: 7
<212> TYPE: PRT
<213> ORGANISM: Artificial Sequence
<220> FEATURE:
<223> OTHER INFORMATION: Ig-IL-2 junction sequence

<400> SEQUENCE: 1

Ser Pro Gly Lys Ala Pro Thr
1               5

<210> SEQ ID NO 2
<211> LENGTH: 4
<212> TYPE: PRT
<213> ORGANISM: Artificial Sequence
<220> FEATURE:
<223> OTHER INFORMATION: Ig C-terminal sequence

<400> SEQUENCE: 2

Ser Pro Gly Lys
1

<210> SEQ ID NO 3
<211> LENGTH: 12
<212> TYPE: DNA
<213> ORGANISM: Artificial Sequence
<220> FEATURE:
<223> OTHER INFORMATION: human gamma-1 heavy chain gene with a silent
      mutation

<400> SEQUENCE: 3
tccccgggta aa                                                         12

<210> SEQ ID NO 4
<211> LENGTH: 42
<212> TYPE: DNA
<213> ORGANISM: Artificial Sequence
<220> FEATURE:
<223> OTHER INFORMATION: 5' oligonucleotide with a Lys to Ala
      substitution

<400> SEQUENCE: 4
ccgggtgcag cacctacttc aagttctaca agaaaacac ag                         42

<210> SEQ ID NO 5
<211> LENGTH: 38
<212> TYPE: DNA
<213> ORGANISM: Artificial Sequence
<220> FEATURE:
<223> OTHER INFORMATION: 3' oligonucleotide with a Lys to Ala
      substitution

<400> SEQUENCE: 5
ctgtgttttc tttgtagaac ttgaagtagg tgctgcac                             38

<210> SEQ ID NO 6
<211> LENGTH: 42
<212> TYPE: DNA
<213> ORGANISM: Artificial Sequence
<220> FEATURE:
<223> OTHER INFORMATION: 5' oligonucleotide with a Lys to Arg
      substitution

<400> SEQUENCE: 6
ccgggtaggg cgccaacttc aagttctaca agaaaacac ag                         42

<210> SEQ ID NO 7
<211> LENGTH: 38
<212> TYPE: DNA
<213> ORGANISM: Artificial Sequence
<220> FEATURE:
<223> OTHER INFORMATION: 3' oligonucleotide with a Lys to Arg
      substitution

<400> SEQUENCE: 7
ctgtgttttc tttgtagaac ttgaagttgg cgccctac                             38

<210> SEQ ID NO 8
<211> LENGTH: 39
<212> TYPE: DNA
<213> ORGANISM: Artificial Sequence
<220> FEATURE:
<223> OTHER INFORMATION: 5' oligonucleotide with a Lys deletion

<400> SEQUENCE: 8
ccgggtgcac ctacttcaag ttctacaaag aaaacacag                                    39

<210> SEQ ID NO 9
<211> LENGTH: 35
<212> TYPE: DNA
<213> ORGANISM: Artificial Sequence
<220> FEATURE:
<223> OTHER INFORMATION: 3' nucleotide with a Lys deletion

<400> SEQUENCE: 9
ctgtgttttc tttgtagaac ttgaagtagg tgcac                                        35

<210> SEQ ID NO 10
<211> LENGTH: 42
<212> TYPE: DNA
<213> ORGANISM: Artificial Sequence
<220> FEATURE:
<223> OTHER INFORMATION: 5' oligonucleotide with a Lys to Gly
      substitution

<400> SEQUENCE: 10
ccgggtgggg ccctacttc aagttctaca agaaaacac ag                                  42

<210> SEQ ID NO 11
<211> LENGTH: 38
<212> TYPE: DNA
<213> ORGANISM: Artificial Sequence
<220> FEATURE:
<223> OTHER INFORMATION: 3' oligonucleotide with a Lys to Gly
      substitution

<400> SEQUENCE: 11
ctgtgttttc tttgtagaac ttgaagtagg ggccccac                                     38

<210> SEQ ID NO 12
<211> LENGTH: 42
<212> TYPE: DNA
<213> ORGANISM: Artificial Sequence
<220> FEATURE:
<223> OTHER INFORMATION: 5' oligonucleotide with a Lys to Leu
      substitution

<400> SEQUENCE: 12
ccgggtctgg cgccaacttc aagttctaca agaaaacac ag                                 42

<210> SEQ ID NO 13
<211> LENGTH: 38
<212> TYPE: DNA
<213> ORGANISM: Artificial Sequence
<220> FEATURE:
<223> OTHER INFORMATION: 3' oligonucleotide with a Lys to Leu
      substitution

<400> SEQUENCE: 13
ctgtgttttc tttgtagaac ttgaagttgg cgccagac                                     38

<210> SEQ ID NO 14
<211> LENGTH: 48

```
<212> TYPE: DNA
<213> ORGANISM: Artificial Sequence
<220> FEATURE:
<223> OTHER INFORMATION: 5' oligonucleotide with a Lys to AlaAlaAla
      substitution

<400> SEQUENCE: 14
ccgggtgcag cagctgcccc aacttcaagt tctacaaaga aaacacag                48

<210> SEQ ID NO 15
<211> LENGTH: 44
<212> TYPE: DNA
<213> ORGANISM: Artificial Sequence
<220> FEATURE:
<223> OTHER INFORMATION: 3' oligonucleotide with a Lys to AlaAlaAla
      substitution

<400> SEQUENCE: 15
ctgtgttttc tttgtagaac ttgaagttgg ggcagctgct gcac                    44

<210> SEQ ID NO 16
<211> LENGTH: 42
<212> TYPE: DNA
<213> ORGANISM: Artificial Sequence
<220> FEATURE:
<223> OTHER INFORMATION: 5' oligonucleotide with a Lys to Cys
      substitution

<400> SEQUENCE: 16
ccgggttgcg caccaacttc aagttctaca agaaaacac ag                       42

<210> SEQ ID NO 17
<211> LENGTH: 38
<212> TYPE: DNA
<213> ORGANISM: Artificial Sequence
<220> FEATURE:
<223> OTHER INFORMATION: 3' oligonucleotide with a Lys to Cys
      substitution

<400> SEQUENCE: 17
ctgtgttttc tttgtagaac ttgaagttgg tgcgcaac                           38

<210> SEQ ID NO 18
<211> LENGTH: 42
<212> TYPE: DNA
<213> ORGANISM: Artificial Sequence
<220> FEATURE:
<223> OTHER INFORMATION: 5' oligonucleotide with a Lys to Asp
      substitution

<400> SEQUENCE: 18
ccgggtgacg caccaacttc aagttctaca agaaaacac ag                       42

<210> SEQ ID NO 19
<211> LENGTH: 38
<212> TYPE: DNA
<213> ORGANISM: Artificial Sequence
<220> FEATURE:
<223> OTHER INFORMATION: 3' oligonucleotide with a Lys to Asp
      substitution

<400> SEQUENCE: 19
ctgtgttttc tttgtagaac ttgaagttgg tgcgtcac                           38

<210> SEQ ID NO 20
<211> LENGTH: 19
<212> TYPE: DNA
```

<213> ORGANISM: Artificial Sequence
<220> FEATURE:
<223> OTHER INFORMATION: sequence at the antibody-IL2 gene fusion
      after linker ligation

<400> SEQUENCE: 20
cccggcatgc gggggtaaa                                              19

<210> SEQ ID NO 21
<211> LENGTH: 6
<212> TYPE: PRT
<213> ORGANISM: Artificial Sequence
<220> FEATURE:
<223> OTHER INFORMATION: sequence at antibody-IL2 fusion junction

<400> SEQUENCE: 21

Pro Ala Cys Gly Gly Leu
1               5

<210> SEQ ID NO 22
<211> LENGTH: 18
<212> TYPE: DNA
<213> ORGANISM: Artificial Sequence
<220> FEATURE:
<223> OTHER INFORMATION: 5' linker sequence

<400> SEQUENCE: 22
gggttcagga tccggagg                                               18

<210> SEQ ID NO 23
<211> LENGTH: 18
<212> TYPE: DNA
<213> ORGANISM: Artificial Sequence
<220> FEATURE:
<223> OTHER INFORMATION: 3' linker sequence

<400> SEQUENCE: 23
cctccggatc ctgaaccc                                               18

<210> SEQ ID NO 24
<211> LENGTH: 9
<212> TYPE: PRT
<213> ORGANISM: Artificial Sequence
<220> FEATURE:
<223> OTHER INFORMATION: sequence at fusion junction

<400> SEQUENCE: 24

Pro Gly Ser Gly Ser Gly Gly Gly Lys
1               5

<210> SEQ ID NO 25
<211> LENGTH: 33
<212> TYPE: DNA
<213> ORGANISM: Artificial Sequence
<220> FEATURE:
<223> OTHER INFORMATION: 5' oligonucleotide with linker

<400> SEQUENCE: 25
gggttcaggc tctggatcag ggtccggatc cgg                              33

<210> SEQ ID NO 26
<211> LENGTH: 33
<212> TYPE: DNA
<213> ORGANISM: Artificial Sequence
<220> FEATURE:
<223> OTHER INFORMATION: 3' oligonucleotide with linker -continued

<400> SEQUENCE: 26
ccggatccgg accctgatcc agagcctgaa ccc                                      33

<210> SEQ ID NO 27
<211> LENGTH: 14
<212> TYPE: PRT
<213> ORGANISM: Artificial Sequence
<220> FEATURE:
<223> OTHER INFORMATION: sequence at fusion junction after linker
      insertion

<400> SEQUENCE: 27

Pro Gly Ser Gly Ser Gly Ser Gly Ser Gly Ser Gly Gly Lys
1               5                   10

<210> SEQ ID NO 28
<211> LENGTH: 25
<212> TYPE: DNA
<213> ORGANISM: Artificial Sequence
<220> FEATURE:
<223> OTHER INFORMATION: 5' oligonucleotide with a Pro to Ala
      substitution

<400> SEQUENCE: 28
cgcagaagag cctctccctg tccgc                                               25

<210> SEQ ID NO 29
<211> LENGTH: 22
<212> TYPE: DNA
<213> ORGANISM: Artificial Sequence
<220> FEATURE:
<223> OTHER INFORMATION: 3' oligonucleotide with a Pro to Ala
      substitution

<400> SEQUENCE: 29
gcggacaggg agaggctctt ct                                                  22

<210> SEQ ID NO 30
<211> LENGTH: 25
<212> TYPE: DNA
<213> ORGANISM: Artificial Sequence
<220> FEATURE:
<223> OTHER INFORMATION: 5' oligonucleotide with a Pro to Leu
      substitution

<400> SEQUENCE: 30
cgcagaagag cctctccctg tccct                                               25

<210> SEQ ID NO 31
<211> LENGTH: 22
<212> TYPE: DNA
<213> ORGANISM: Artificial Sequence
<220> FEATURE:
<223> OTHER INFORMATION: 3' oligonucleotide with a Pro to Leu
      substitution

<400> SEQUENCE: 31
agggacaggg agaggctctt ct                                                  22

<210> SEQ ID NO 32
<211> LENGTH: 25
<212> TYPE: DNA
<213> ORGANISM: Artificial Sequence
<220> FEATURE:
<223> OTHER INFORMATION: 5' oligonucleotide with a Pro to Gly
      substitution

```
-continued

<400> SEQUENCE: 32
cgcagaagag cctctccctg tccgg                                          25

<210> SEQ ID NO 33
<211> LENGTH: 22
<212> TYPE: DNA
<213> ORGANISM: Artificial Sequence
<220> FEATURE:
<223> OTHER INFORMATION: 3' oligonucleotide with a Pro to Gly
      substitution

<400> SEQUENCE: 33
ccggacaggg agaggctctt ct                                             22

<210> SEQ ID NO 34
<211> LENGTH: 9
<212> TYPE: PRT
<213> ORGANISM: Artificial Sequence
<220> FEATURE:
<223> OTHER INFORMATION: Ig-TNF junction sequence

<400> SEQUENCE: 34

Ser Pro Gly Lys Val Arg Ser Ser Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Ig-(deleted Lys)-TNF fusion sequence

<400> SEQUENCE: 35

Ser Pro Gly Val Arg Ser Ser Ser
1               5
```